US006821946B2

(12) United States Patent
Goldspink et al.

(10) Patent No.: US 6,821,946 B2
(45) Date of Patent: Nov. 23, 2004

(54) REPAIR OF NERVE DAMAGE

(75) Inventors: Geoffrey Goldspink, London (GB); Giorgio Terenghi, London (GB)

(73) Assignees: University College London, London (GB); East Grinstead Medical Research Trust, East Grinstead (GB)

( * ) Notice: Subject to any disclaimer, the term of this patent is extended or adjusted under 35 U.S.C. 154(b) by 0 days.

(21) Appl. No.: 09/852,261

(22) Filed: May 10, 2001

(65) Prior Publication Data

US 2002/0083477 A1 Jun. 27, 2002

(30) Foreign Application Priority Data

May 10, 2000 (GB) .............................................. 0011278

(51) Int. Cl.⁷ ........................... A61K 38/00; C07K 5/00
(52) U.S. Cl. .......................................... 514/2; 530/300
(58) Field of Search ............................. 514/2; 530/300, 530/350; 536/23.5; 424/198.1

(56) References Cited

U.S. PATENT DOCUMENTS

| 5,650,496 A | 7/1997 | Brierley et al. |
| 5,776,897 A | 7/1998 | Lewis et al. |
| 6,221,842 B1 * | 4/2001 | Goldspink .................... 514/12 |

FOREIGN PATENT DOCUMENTS

| EP | 0 229 750 | 7/1987 |
| EP | 0 308 386 A1 | 3/1989 |
| WO | WO 92/11865 | 7/1992 |
| WO | WO 92/19256 | 11/1992 |
| WO | WO 93/09236 | 5/1993 |
| WO | WO 93/10806 | 6/1993 |
| WO | WO 95/13290 | 5/1995 |
| WO | WO 97/33997 | 9/1997 |
| WO | WO 01/36483 A1 | 5/2001 |

OTHER PUBLICATIONS

Jackowski "Neural injury repair: hope for the future as barriers to effective CNS regeneration become clearer." British Journal o Neurosurgery 9: 303–317.*
Hameed et al. "Expression of IGF–I splice variants in young and old human skeletal muscle after high resistance exercise." The Journal of Physiology 547(Pt. 1): 247–254.*
Goldspink and Yang (Dec. 2001) "Effects of Activity on Growth Factor Expression." International Journal of Sport Nutritio and Exercise Metabolism 11: S21–S27.*
Doerks et al., (Jun. 1998) "Protein annotation: detective work for function prediction." Trends in Genetics 14(6): 248–250.*
Smith and Zhang (Nov. 1997) "The challenges of genome sequence annotation or 'The devil is in the details'." Nature Biotechnology 15:1222–1223.*
Brenner (Apr. 1999) "Errors in genome annotation." Trends in Genetics 15(4): 132–133.*
Bork and Bairoch (Oct. 1996) "Go hunting in sequence databases but watch out for the traps." Trends in Genetics 12(10): 425–427.*
Wells (Sep. 18, 1990) "Additivity of Mutational Effects in Proteins." Biochemistry 29(37): 8509–8517.*
Ngo et al. (Mar. 2, 1995) "The Protein Folding Problem and Tertiary Structure Prediction, Chapter 14: Computational Complexity Protein Structure Prediction, and the Levinthal Paradox" pp. 492–495.*
Bork (2000) "Powers and Pitfalls in Sequence Analysis: The 70% Hurdle." Genome Research 10:398–400.*
Skolnick and Fetrow (2000) "From gene to protein structure and function: novel applications of computational approaches in th genomic era." Trends in Biotech. 18(1): 34–39.*
Wells Addivity of Mutational Effects in Proteins (1990) Biochemistry (29): 37, 8509–8517.*
Ngo et al. Computational Complexity, Protein Structure Prediction, and the Levinthal Paradox (1994) The Protein Folding Problem and Teriary Structure Prediction (#14), 491–495.*
Morishita, et al., "Pluronic® F–127 gels incorporating highly purified unsaturated fatty acids for buccal delivery of insulin", International Journal of Pharmaceutics 212 (2001) 289–293.
Harazi et al;"A resorbable nerve conduit as an alternative to nerve autograft in nerve gap repair"; British Journal of Plastic Surgery; (1999) vol. 52; pp 1–5.
Hope; "Implant that could make damaged nerves work again"; Daily Mail; (Aug. 18, 1999); 1 page.
Hobson et al; "VEGF enhances intraneural angiogenesis and improves nerve regeneration after axotomy"; J. Anatomy; (2000) vol. 197; pp 591–605.
Simon et al; "Differential effects of NT–3 on reinnervation of the fast extensor digitorum longus (EDL) and the slow soleus muscle of rat"; European Journal of Neuroscience, (2000); vol. 12; pp. 863–871.
Ahmed et al; "Nerve growth factor enhances peripheral nerve regeneration in non–human primates"; Scand J. Plast. Reconstr. Hand Surg. (1999) vol. 33: pp 393–401.
Hazari et al; "A new resorbable wrap–around implant as an alternative nerve repair technique"; Journal of Hand Surgery; (1999) 24B: 3; pp 291–295.

(List continued on next page.)

*Primary Examiner*—Elizabeth Kemmerer
*Assistant Examiner*—Christopher James Nichols
(74) *Attorney, Agent, or Firm*—Nixon & Vanderhye P.C.

(57) ABSTRACT

The invention provides a method of treating nerve damage involving administering to the damaged nerve an effective non-toxic amount of an MGF (mechano-growth factor) Insulin-like Growth Factor I (IGF-I) isoform which includes amino acid sequences encoded by nucleic acid sequences of IGF-I exons 4, 5 and 6 in the reading frame of MGF and having the ability to reduce motoneurone loss by 20% or greater in response to nerve avulsion.

23 Claims, 11 Drawing Sheets

OTHER PUBLICATIONS

Wiberg et al; "Primary sensory neuron survival following targeted administration of nerve growth factor to an injured nerve"; Scand. J. Plast. Reconstr. Hand Surg. (1999) vol. 33: 387–392.

Sterne et al; "NT–3 modulates NPY expression in primary sensory neurons following peripheral nerve injury"; J. Anatomy; (1998); vol. 193; pp. 273–281.

Sterne et al; "Neurotrophin–3–enhanced nerve regeneration selectively improves recovery of muscle fibers expressing myosin heavy chains 2b"; J. of Cell Biology; (1997); vol. 139; pp 709–715.

Sterne et al; Neurotrophin–3 delivered locally via fibronectin mats enhances peripheral nerve regeneration; European Journal of Neuroscience; (1997); vol. 9 pp 1388–1396.

Whitworth et al; "Nerve growth factor enhances nerve regeneration through fibronectin grafts; Journal of Hand Surgery"; (1996); 24B: 4: pp. 514–522.

Whitworth et al; "Targeted delivery of nerve growth factor via fibronectin conduits assists nerve regeneration in control and diabetic rats"; European Journal of Neurosciences; (1995); vol. 7; pp 2220–2225.

Whitworth et al; "Oriented mats of fibronectin as a conduit material for use in peripheral nerve repaid"; Journal of Hand Surgery; (1995); 20B; 4; pp 429–436.

Siegfried et al; "A mitogenic peptide amide encoded within the E peptide domain of the insulin–like growth factor IB prohormone"; PNAS; (1992); vol. 89; pp 8107–8111.

Ido et al; "Prevention of vascular and neural dysfunction in diabetic rats by C–peptide"; Science; (1997); vol 277; pp 563–566.

Tian et al; "Recombinant E–peptides of pro–IGF–I have mitogenic activity"; Endocrinology; (1999)vol. 140; pp 3387–3390.

Stewart et al; "Growth, differentiation; and survial: multiple physiological functions for insulin–like growth factors"; Physiological Revs.; (1996); vol. 76; No. 4; pp 1005–1026.

Goldspink et al; "Muscle growth in response to mechanical stimuli"; American Physiological Society; (1995); vol. 268, No. 2; pp E288–E297.

Edwall et al; "Induction of insulin–like growth factor I messenger ribonucleic acid during regeneration of rat skeletal muscle"; Endocrinology; (1989); vol. 124; No. 2; pp 820–825.

DeVol et al; "Activation of insulin–like growth factor gene expression during work–induced skeletal muscle growth"; American Journal of Physiology; (1990) vol. 259, No. 2; pp E89–E–95.

Lowe et al; "Distribution and Regulation of rat insulin–like growth factor I messenger ribonucleic acids encoding alternative carboxyterminal E–peptides: evidence for differential processing and regulation in liver"; Molecular Endocrinology; (1998); vol. 2. No. 6; pp. 528–535.

Han et al; "Cell localization of somatornedin (insulin–like growth factor) messenger RNA in the human fetus"; Science; (1987); vol. 236; 6 pages.

Jansen et al; "Sequence of cDNA encoding human insulin–like growth factor I precursor"; Nature; (1983); vol. 306; pp 609–611.

Goldspink et al; "Gene expression in skeletal muscle in response to stretch and force generation" American Physiological Society; (1992); 262; pp R356–R363.

Goldspink et al; "The effect of hypokinesia and hypodynamia on protein turnover and the growth of four skeletal muscles of the rat"; European Journal of Physiology; (1986); 407; pp 333–340.

Valenzuela et al; "Receptor tyrosine kinase specific for the skeletal muscle lineage: expression in embryonic muscle, at the neuromuscular junction, and after injury"; Neuron; (1995); vol. 15; pp 573–584.

Goldspink et al, "Local Growth Regulation . . . ", Journal of Physiology, vol. 495P, Jul. 2, 1996, pp. 162P–163P, XP000677210.

Johnson et al, "Rescue of Injured Adult . . . ", Society for Neuroscience Abstracts, vol. 26, No. 1–2, 2000, pp. Abstract No. –792.3, XP001029877.

Vaught et al, "Potential utility of rhIGF–1 . . . ", Symposium on Growth factors as drugs fro neurological and sensory disorders held at the Ciba Foundation, London, Apr. 25–27, 1995, pp. 18–38.

Tuszynski et al, "Somatic gene therapy for nervous . . . ", Symposium on Growth factors as drugs for neurological and sensory disorders held at the Ciba Foundation, London, Apr. 25–27, 1995, pp. 85–97.

Tan et al, "The Problems of Delivering Neuroactive . . . ", Symposium on Growth factors as drugs for neurological and sensory disorders held at the Ciba Foundation, London, Apr. 25–27, 1995, pp. 211–239.

Apfel et al, "Neurotrophic factors in the treatment . . . ", Symposium on Growth factors as drugs for neurological and sensory disorders held at the Ciba Foundation, London, Apr. 25–27, 1995, pp. 98–112.

Chew et al, Endocrinology 136, No. 5 (1995).

Hazari et al, British J. Plastic Surgery 52, 653–57, (1999).

Jansen et al, Mol. Cell Endocrinology 78:115–25 (1991).

Lundborg et al, J. Hand Surgery 22:99–106 (1997).

Mañes et al, Endocrinology 138:905–915 (1997).

McKoy et al, J. Physiol. 516.2, 583–592 (1999).

Rotwein et al, J. Biol. Chem. 261:4828–3 (1986).

Skarli et al, J. Physiol. 509.8, 192.8 (1998).

Tobin et al, Mol. Endocrinology 1914–20 (1990).

Vejsada et al, Eur. J. Neurosci; 7:108–115 (1995).

Vesjada et al, Neuroscience 84:129–139 (1998).

Yang et al, Journal of Muscle Cell Research and Cell Motility 4:487–496 (1996).

Goldspink, J. Anat. No. 3, 194:323–334 (1999).

Goldspink et al, J. Physiol. 495:162–163 (1996).

Rotwein, P., PNAS 83:77–81 (1986).

Caroni, P., et al., J. Neuroscience, No. 5, Part 2, 14:3378–3388 (1994).

Caroni, P. et al, J. Cell Biol., No. 4, 125:893–902 (1994).

Doré et al, Trends in Neurosci., No. 8, 20:326–331 (1997).

Alila, H., et al, Human Gene Therapy, No. 5, 8:1785–1795 (1997).

* cited by examiner

Avulsion

Avulsion

Avulsion

Plasmid

Plasmid

Plasmid

MGF Plasmid

MGF Plasmid

MGF Plasmid

Fig.5.

cDNA sequence of Human MGF

Exon 3
Exon 4
GGACCGGAGACGCTCTGCGGGGCTGAGCTGGTGATGCTCTTCAGTTCGTGTGTGGAGACAGGGGCTTTTATTTCAACAAGCCCACAGGGTATGCTCCAGCAGTCGG AGGGGCGCCTCAGACACAGGCATCGTGGATGAGTGCTGCTTCCGGAGCTGTGATCTAAGGAGGCTGGAGATGTATTGCGCACCCCTCAAGCCTGCCAAGTCAGCTCGCTC Exon 5
Exon 6
TGTCCGTGCCCAGCGCCACCGCCCAAGAACATGCCCAAGACCCAGAAGTATCAGCCCCCATCTACCAACAAGAACACGAAGTCTCAGAGAAGGAAGTACATTTGAAG .ACACAAGTAGAGGGAGTGCAGGAAACAAGAACTACAGGATGTAGAAGACACCCTTCTGAGGAGTGAAGAAGGACAGGCCACCGCGCAGGACCCTTTGCTCTGCACAGTTA CCTGTAAACATTGGAATACCGGCCAAAAAATAAGTTTGATCACATTTCAAAGATGGCATTTCCCCAATGAAATACACAAGTAAACAT

Protein sequence of Human MGF

Exon 3
Exon 4
GlyProGluThrLeuCysGlyAlaGluLeuValAlaAspAlaLeuGlnPheValCysGlyAspArgGlyPheTyrPheAsnLysProThrGlyTyrGlySerSerSerAr gArgAlaProGlnThrGlyIleValAspGluCysCysPheArgSerCysAspLeuArgArgLeuGluMetTyrCysAlaProLeuLysProAlaLysSerAlaArgS Exon 5
Exon 6
erValArgAlaGlnArgHisThrAspMetProLysThrGlnLysTyrGlnProProSerThrAsnLysAsnThrLysSerGlnArgArgLysGlySerThrPheGlu GluHisLys

Fig.6.

cDNA sequence of Rat MGF

Exon 3
GGACCAGAGACCCTTTGCGGGGCTGAGCTGTGTGAGCGCTCTTCAGTTCGTGTGTGACCAAGGGCTTTTACTTCAACAAGCCCACAGTCTATGGCTCCAGCATTCG Exon 4
GAGGGCACCACAGACGGGCATTGTGGATGAGTGTTGCTTCCGGAGCTGTGATCTGAGGAGGCTGGAGATGTACTGTGTCCGCTGCAAGCCTACAAAGTCAGCTCGTT Exon 5
CCATCCGGGCCCAGGCCCACACTGACATGCCCAAGACTCAGAAGTCCCAGCCTCTGAGCACACACAAGAAAAGGAAGCTGCAAGGAGAAGGAAAGGAAGTACACTT GAAGAACACAAGTAGAGGAAGTGCAGGAAACAAGACCTACAGAATGTAGGAGGAGCCTCCCGAGGAACAGAAAATGCCACGTCACCGCAAGATCCTTTGCTGCTTGA Exon 6
GCAACCTGCAAAACATCGGAACACCTGCCAAATATCAATAATGAGTTCAATATCATTTCAGAGATGGGCATTTCCCTCAATGAAATACACAAGTAAACATTCCCGGA

ATTC

Protein sequence of Rat MGF

Exon 3
GlyProGluThrLeuCysGlyAlaGluLeuValAlaAspAlaLeuGlnPheValCysGlyProArgGlyPheTyrPheAsnLysProThrValTyrGlySerSerIleAr Exon 4
gArgAlaProGlnThrGlyIleValAspGluCysCysPheArgSerCysAspLeuArgArgLeuGluMetTyrCysValArgCysLysProThrLysSerAlaArgS Exon 5
erIleArgAlaGlnArgHisThrAspMetProLysThrGlnLysSerGlnProLeuSerThrHisLysLysArgLysLeuGlnArgArgLysGlySerThrLeu Exon 6
GluGluHisLys

Fig.7.

cDNA sequence of Rabbit MGF

Exon 3
GGACCGGAGAGACGCTCTGCGGTGCTGAGCTGGTGGATGCTCTTCAGTTCGTGTGTGGAGACAGGGGCTTTTATTTCAACAGCCCACAGATACGGCTCCAGCAGTCGGAGGCACC Exon 4
TCAGACAGGCATCGTGGATGAGTGCTGCTTCCGGAGCTGTGATCTGGAGATGTACTGTGCACCCCTCAAGCGGCAAAGGCAGCCCGCTCCGTCCGTGCCCAGCGCC Exon 5
ACACCGACACATGCCCAAGACTCAGAAGTATCAGCCTCCATCTACCAACAAGAAATGAAGTCTCAGAGGAGAAGGAAGTACATTTGAAGAACACAAGTAGAGGGAGTGCAGG Exon 6
AAACAAGAACTACAGAGATGTAGGAAGACCCTTCTGAGGAGTGAAGAAGGACAGGCCACCGCAGGAGACCCCTTTGCTCTGCACAGTTACCTGTAAACATTGGAATACCGGCCAAAAAAT

AAGTTTGATCACATTTCAAAGATGGCATTTCCCCCAATGAAATACACAAGTAAACATTC

Protein sequence of Rabbit MGF

Exon 3
GlyProGluThrLeuCysGlyAlaGluLeuValAspAlaLeuGlnPheValCysGlyAspArgGlyPheTyrPheAsnLysProThrGlyTyrGlySerSerArgArgAlaPr Exon 4
oGlnThrGlyIleValAspGluCysCysPheArgSerCysAspLeuArgArgLeuGluMetTyrCysAlaProLeuLysAlaAlaArgSerValArgAlaGlnArgH Exon 5
isThrAspMetProLysThrGlnLysTyrGlnProProSerThrAsnLysLysMetLysSerGlnArgArgArgLysGlySerThrPheGluGluHisLys Exon 6

Fig.8.

cDNA sequence of Human L.IGF-1

Exon 3
GGACCGGAGACGCTCTGCGGGGCTGAGCTGGTGGATGCTCTTCAGTTCGTGTGTGGAGACAGGGGCTTTTATTTCAACAGCCCACAGGGTATGGCTCCAGCAGTCGGAGGGCGCC Exon 4
TCAGACAGGCATCGTGGATGAGTGCTGCTTCCGGAGCTGTGATCTAAGGAGGCTGGAGATGTATTGCGCACCCCTCAAGCCTGCCAAGTCAGCTCGCTCTGTCCGTGCCCAGCGCC Exon 6
ACAC GACATGCCCAAGACCCAGAAGGAAGTACATTTGAAGAACGCAAGTAGAGGGAGTGCAGGAAACAAGAACTACAGGATGTAG Protein sequence of Human L.IGF-1

Exon 3                                                                                                      Exon 4
GlyProGluThrLeuCysGlyAlaGluLeuValAlaAspAlaLeuGlnPheValCysGlyAspArgGlyPheTyrPheAsnLysProThrGlyTyrGlySerSerArgArgAlaPr oGlnThrGlyIleValAspGluCysCysPheArgSerCysAspLeuArgArgLeuGluMetTyrCysAlaProLeuLysProAlaLysSerAlaArgSerValArgAlaGlnArgH Exon 6
isThrAspMetProLysThrGlnLysGluValHisLeuLysAsnAlaSerArgGlySerAlaGlyAsnLysAsnTyrArgMet

Fig.9.

cDNA sequence of Rat L.IGF-1

Exon 3
GGACCAGAGACCCTTTGCGGGGCTGAGCTGTGGACGCTCTTCAGTTCGTGTGGACCAAGGGGCTTTTACTTCAACAAGCCCACAGTCTATGCTCCAGCATTCGGAGGGCACC Exon 4
ACAGACGGGCATTGTGGATGAGTGTTGCTTCCGGAGCTGTGATCTGAGGAGGCTGGAGATGTACTGTGTCCGCTGCAAGCCTACAAAGTCAGCTCGTTCCATCCGGGCCAGGCC Exon 6
ACACTGACATGCCCAAGACTCAGAAGGAAGTACACTTGAAGAACACAAGTAGAGGAAGTGCAGGAAACAGACCTACAGAATGTAGGAGGAGCCTCCCGAGAACAGAAAATGCCA CGTCACCGCAAGATCCTTTGCTGCTTGAGCAACCTGCAAACATCGGAACACCTGCCAAATATCAATAATGAGTTCAATATCATTTCAGAGATGGGCATTCCCTCAATGAAATAC

ACAAGTAAACATTCCCGGAATTC

Protein sequence of Rat L.IGF-1

Exon 3                                                                    Exon 4
GlyProGluThrLeuCysGlyAlaGluLeuValAlaAspAlaLeuGlnPheValCysGlyProArgGlyPheTyrPheAsnLysProThrValTyrGlySerIleArgArgAlaPr Exon 6
oGlnThrGlyIleValAspGluCysCysPheArgSerCysAspLeuArgArgLeuGluMetTyrCysValArgCysLysProThrLysSerAlaArgSerIleArgArgAlaGlnArgH isThrAspMetProLysThrGlnLysGluValHisLeuLysAsnThrSerArgGlySerAlaGlyAsnLysThrTyrArgMet

Fig.10.

cDNA sequence of Rabbit L.IGF-1

Exon 3
GGACCGGAGAGCGCTCTGCGGTGCTGAGCTGGTGGATGCTCTTCAGTTCGTCGTGTGGAGACAGGGGCTTTTATTTCAACAAGCCCACAGGATACGGCTCCAGCAGTCGGAGGGCACC Exon 4
TCAGACAGGCATCGTGGATGAGTGCTGCTTCCGGAGCTGTGATCTGAGGAGGCTGGAGATGTACTGTGCACCCCTCAAGCCGGCAAAGGCAGCCCGCTCCGTCCGTGCCCAGCGCC Exon 6
ACACCGACATGCCCAAGACTCAGAAGGAAGTACATTTGAAGAGAACACAAGTAGAGGGAGTGCAGGAAACAAGAACTACAGGATGTGAGGAAGACCCTTCTGAGGAGTGAAGAAGGACA GGC ACCGCAGGAGACCCCTTTGCTCTGCACAGTTACCTGTAAACATTGGAATACCGGCCAAAAAATAAGTTTGATCACATTTCAAAGATGGCATTTCCCCCAATGAAATACACAAGTA

AACATTC

Protein sequence of Rabbit L.IGF-1

Exon 3
GlyProGluThrLeuCysGlyAlaGlnPheValCysGlyAspArgGlyPheTyrPheAsnLysProThrGlyTyrGlySerSerArgArgAlaPr Exon 4
pGlnThrGlyIleValAspGluCysCysPheArgSerCysAspLeuArgArgLeuGluMetTyrCysAlaProLeuLysProAlaLysAlaAlaArgSerValArgAlaArgGlnArgH Exon 6
isThrAspMetProLysThrGlnLysGluValHisLeuLysAsnThrSerArgGlySerAlaGlyAsnLysAsnTyrArgMet

Fig. 11.

Exon 4

```
Hu  MGF  - A | sn Lys Pro Thr Gly Tyr Gly Ser Ser Ile Arg Arg Ala Pro Gln Thr Gly Ile Val Asp Glu Cys Cys Phe
Rat MGF  - A | sn Lys Pro Val Tyr Gly Ser Ser Ile Arg Arg Ala Pro Gln Thr Gly Ile Val Asp Glu Cys Cys Phe
Rab MGF  - A | sn Lys Pro Thr Tyr Gly Ser Ser Ile Arg Arg Ala Pro Gln Thr Gly Ile Val Asp Glu Cys Cys Phe
Hu  IGF  - A | sn Lys Pro Thr Gly Tyr Gly Ser Ser Ser Arg Arg Ala Pro Gln Thr Gly Ile Val Asp Glu Cys Cys Phe
Rat IGF  - A | sn Lys Pro Val Tyr Gly Ser Ser Ile Arg Arg Ala Pro Gln Thr Gly Ile Val Asp Glu Cys Cys Phe
Rab IGF  - A | sn Lys Pro Thr Gly Tyr Gly Ser Ser Ser Arg Arg Ala Pro Gln Thr Gly Ile Val Asp Glu Cys Cys Phe

Hu  MGF  - Arg Ser Cys Asp Leu Arg Arg Leu Glu Met Tyr Cys Ala Pro Leu Lys Pro Ala Lys Ser Ala Arg Ser Val
Rat MGF  - Arg Ser Cys Asp Leu Arg Arg Leu Glu Met Tyr Cys Val Arg Cys Lys Pro Thr Lys Ser Ala Arg Ser Ile
Rab MGF  - Arg Ser Cys Asp Leu Arg Arg Leu Glu Met Tyr Cys Ala Pro Leu Lys Pro Ala Lys Ser Ala Arg Ser Val
Hu  IGF  - Arg Ser Cys Asp Leu Arg Arg Leu Glu Met Tyr Cys Ala Pro Leu Lys Pro Ala Lys Ser Ala Arg Ser Val
Rat IGF  - Arg Ser Cys Asp Leu Arg Arg Leu Glu Met Tyr Cys Val Arg Cys Lys Pro Thr Lys Ser Ala Arg Ser Ile
Rab IGF  - Arg Ser Cys Asp Leu Arg Arg Leu Glu Met Tyr Cys Ala Pro Leu Lys Pro Ala Lys Ala Arg Ser Val
```

Exon 5

```
Hu  MGF  - Arg Ala Gln Arg His Thr Asp Met Pro Lys Thr Gln Lys | Tyr Gln Pro Pro Ser Thr Asn Lys Asn Thr Lys
Rat MGF  - Arg Ala Gln Arg His Thr Asp Met Pro Lys Thr Gln Lys | Ser Gln Pro Leu Ser Thr His Lys Lys Arg Lys
Rab MGF  - Arg Ala Gln Arg His Thr Asp Met Pro Lys Thr Gln Lys | Tyr Gln Pro Pro Ser Thr Asn Lys Lys Met Lys
Hu  IGF  - Arg Ala Gln Arg His Thr Asp Met Pro Lys Thr Gln Lys |
Rat IGF  - Arg Ala Gln Arg His Thr Asp Met Pro Lys Thr Gln Lys |
Rab IGF  - Arg Ala Gln Arg His Thr Asp Met Pro Lys Thr Gln Lys |
```

Exon 6

```
Hu  MGF  - Ser Gln     Arg Arg Lys G | ly Ser Thr Phe Glu Glu His Lys
Rat MGF  - Leu Gln Arg Arg Arg Lys G | ly Ser Thr Leu Glu Glu His Lys
Rab MGF  - Ser Gln Arg Arg Arg Lys G | ly Ser Thr Phe Glu Glu His Lys
Hu  IGF  -                           | Glu Val His Leu Lys Asn Ala Ser Arg Gly Ser Ala Gly Asn Lys Asn Tyr Arg Met
Rat IGF  -                           | Glu Val His Leu Lys Asn Thr Ser Arg Gly Ser Ala Gly Asn Lys Thr Tyr Arg Met
Rab IGF  -                           | Glu Val His Leu Lys Asn Thr Ser Arg Gly Ser Ala Gly Asn Lys Asn Tyr Arg Met
```

REPAIR OF NERVE DAMAGE

FIELD OF THE INVENTION

The present invention concerns the treatment of nerve damage with the Insulin-like Growth Factor I (IGF-I) isoform known as mechano growth factor (MGF). More particularly, MGF is localised around the sites of such damage to effect repair, typically by means of the placement of a conduit around the two ends of a severed peripheral nerve,

BACKGROUND OF THE INVENTION
IGF-I and MGF

Mammalian IGF-I polypeptides have a number of isoforms, which arise as a result of alternative mRNA splicing. Broadly, there are two types of isoform, liver-type isoforms and non-liver ones. Liver-type isoforms may be expressed in the liver or elsewhere but, if expressed elsewhere, are equivalent to those expressed in the liver. They have a systemic action and are the main isoforms in mammals. Non-liver isoforms are less common and some are believed to have an autocrine/paracrine action. A cDNA of the latter type has been cloned, as discussed below, following detection in skeletal and cardiac muscle undergoing mechanical overload.

The terminology for the IGF-I splice variants is based on the river isoforms (Chew et al, 1995) and has not fully evolved to take into account those produced by non-liver tissues The latter are controlled to some extent by a different promoter (promoter 1) to the liver IGP-I isoforms, which respond to hormones and are under the control of promoter 2 (Layall, 1996).

For the purposes of this invention, two isoforms are of particular interest. These are both expressed in skeletal muscle, though it has only recently been appreciated that two muscle isoforms exist. The first isoform is muscle liver-type IGF-I or L.IGF-I (systemic type), which is of interest mainly for comparative purposes. The second is mechano-growth factor or MGF (autocrine/paracrine type).

These are alternative splice variants. Exons 1 and 2 are alternative leader exons (Tobin et al, 1990; Jansen et al, 1991) with distinct transcription start sites which are differentially spliced to common exon 3. Exons 3 and 4 code for the mature IGF-I peptide (B, C, A and D domains) as well as the first 16 amino acid of the E domain. Exons 5 and 6 each encodes an alternative part of a distinct extension peptide, the E domain. This is followed by the termination codons of precursor IGF-I, 3' untranslated regions and poly(A) addition signal sites (Rotwein et al, 1986). A further difference between the two isoforms is that MGF is not glycosylated and is therefore smaller. It has also been shown to be less stable. It may thus have a shorter half-life.

It has been shown that MGF, which is not detectable in skeletal muscle unless it is subjected to exercise or stretch (Yang et al, 1996), has exons 4, 5 and 6 whilst the muscle L.IGF-I has exons 4 and 6. Exon 5 in MGF has an insert of 52 bp which changes the 3' reading frame and hence the carboxy end of the peptide In addition, MGF has been detected in overloaded cardiac muscle (Skarli et al, 1998).

Functional epitope mapping of IGF-I using a battery of monoclonal antibodies (Mañes et al, 1997) has shown that the carboxy terminus (3' end) of IGF-I is important in determining the affinity of the peptide for a particular receptor and/or binding protein.

MGF mRNA is not detected in dystrophic muscle even when it is subjected to stretch. The inability of muscle in both the autosomal- and dystrophin-deficient dystrophies to respond to overload by stretch (Goldspink et at, 1996) indicates that the cytoskeleton may be involved in the transduction mechanism. It is probable that there is a basic mechanism that detects muscle overload and which results in the expression of both variant forms of IGF.

Thus, MGF is known to be expressed in skeletal and cardiac muscle tissue in response to stretch and exercise and as a result is believed to be involved in repair of damage to muscle (Yang et al, 1996; WO97/33997). This has been confirmed more recently by McKoy et at (1999).

Conduits

It has previously been proposed to use a conduit to assist in nerve damage repair, e.g. to bridge a gap in a severed nerve. The aim is to place the conduit around the nerve, e.g. around its two severed ends, so that the nerve will regrow within the conduit.

In particular, conduits composed of Poly-3-hydroxybutyrate have been proposed as an alternative to nerve autografts, which result in sub-optional functional results and donor site morbidity. PHB occurs within bacterial cytoplasm as granules and is available as bioabsorbable sheets. PHB conduits have been shown to assist in nerve regeneration and to show good results compared to nerve autografts (Hazari et al, J. Plastic Surgery (1999)).

Various different conduit materials have been proposed, including PHB, but none have yet been fully applied clinically. Only silicone has been applied, in a restricted clinical trial (Lundborg et al, 1997), but a second operation has sometimes been necessary to remove the non-resorbable silicone tube.

SUMMARY OF THE INVENTION

We have now identified a new and surprising property of MGF.

Plasmids containing MGF DNA operably linked to expression signals capable of securing expression in muscles were prepared and injected intramuscularly into rats. Expression of MGP in vivo resulted. To investigate the effect of MGF on the animal's nerves, the right-facial nerve was damaged by avulsion in some animals and crushing in others. Similar experiments were performed with plasmids capable of expressing L.IGF-I and control experiments were also carried out using equivalent "empty" plasmids lacking an MGF or L.IGF-I coding sequence, and with non-operated rats.

The surgical procedures carried out normally result in massive motoneurone loss, and that was the case in the control animals. However, in the case of nerve avulsion, use of L.IGF-I reduced motoneuron loss to about 50% and use of MGF reduced motoneurone loss to about 20%. Although both isoforms were found to be effective in promoting motoneurone rescue, MGF was, surprisingly, more than twice as effective as L.IGF-I. This opens up the possibility of using MGF in the treatment of neurological disorders, especially motoneurone disorders. Additionally, it should be noted that this is the first time that altered availability of neurotrophic factors to intact adult motoneurones has been shown to affect a subsequent response to injury and also that this is the first time that intramuscular gene transfer using plasmid DNA has been shown to be an effective strategy for motoneuronal rescue.

IGF-I isoforms have specific binding proteins which determine their action, particularly in terms of which tissues the isoform takes effect in. It appears that the binding protein for MGF is located in the central nervous system (CNS) as well as in skeletal and cardiac muscle. This may explain its greater effectiveness. Also, the fact that MGF is not glycosylated and thus smaller than L.IGF-I may facilitate its transfer from the muscle to the motor neuron cell bodies in the CNS.

These findings have general applicability to the treatment of neurological disorders and are surprising because MGF had previously only been detected in cardiac muscle and skeletal muscle under stretch/exercise. Chew (1995) suggests that an IGF-I Ec form is found in the liver. However, this is detectable in very low amounts and may be due to leaky transcription. Therefore, it had previously been believed that MGF was a muscle-specific isoform whereas it has now emerged that it is also implicated in repairing damage to the nervous system and can thus form the basis of treatments for disorders of the nervous system.

Moreover, our findings show that MGF will be useful in repairing nerve damage, especially in the peripheral nervous system (PNS), when localised around the site of the damage. In particular, MGF will be useful in repairing nerve damage in conjunction with a conduit placed around the two ends of a severed nerve. Notably, we have found that, by placing the two ends of a severed rat sciatic nerve in juxtapostion in a conduit and filling with a gel comprising a vector containing MGF cDNA, repair of a 3 mm gap in the nerve was achieved in as little as two weeks. The properties of MGF in nerve regeneration, as identified by the present Inventors, can be combined with the tendency of such conduits to facilitate nerve regeneration. This will result in an improved conduit-based means of repairing nerve damage. Other means of localising MGF at the site of damage can also be used.

Accordingly, the invention provides:

a method of treating nerve damage comprising administering to a subject in need thereof an effective non-toxic amount of an MGF (mechano-growth factor) Insulin-like Growth Factor I (IGF-I) isoform comprising amino acid sequences encoded by nucleic acid sequences of IGF-I exons 4, 5 and 6 in the reading frame of MGF and having the ability to reduce motoneurone loss by 20% or greater in response to nerve avulsion, by localisation of said MGF at the site of said damage.

The invention also provides:

a kit for the treatment of nerve damage comprising:
(a) an MGF IGF-I isoform of the invention; and
(b) a conduit of the invention; and optionally
(c) a polypeptide growth factor which prevents or diminishes degeneration; and optionally
(d) another neurologically active agent.

BRIEF DESCRIPTION OF THE DRAWINGS

FIG. 5: cDNA and amino acid sequence of human MGF, showing its exon Structure (SEQ ID NOs: 1 and 2 respectively)

FIG. 6: cDNA and amino acid sequence of rat MGF, showing its exon Structure (SEQ ID NOs: 3 and 4 respectively)

FIG. 7: cDNA and amino acid sequence of rabbit MGF, showing its exon Structure (SEQ ID NOs: 5 and 6 respectively)

FIG. 8: cDNA and amino acid sequence of human L.IGF-I, showing its exon structure (SEQ ID NOs: 9 and 10 respectively)

FIG. 9: cDNA and amino acid sequence of rat L-IGF-I, showing its exon structure (SEQ ID NOs: 11 and 12 respectively)

FIG. 10: cDNA and amino acid sequence of rabbit L-IGF-I, showing its exon structure (SEQ ID NOs: 13 and 14 respectively)

FIG. 11: Sequence alignment, illustrating exon structure of human, rat and rabbit MGF (amino acids 26–110 of SEQ ID NO:2, amino acids 26–111 of SEQ ID NO:4, and amino acids 26–111 of SEQ ID NO:6, respectively and human, rat and rabbit L-IGF-I (amino acids 26–105 of SEQ ID NO:10, amino acids 26–105 of SEQ ID NO:12, and amino acids 26–105 of SEQ ID NO:14, respectively), and highlighting similarities and differences.

DETAILED DESCRIPTION OF THE INVENTION

Figure 1:
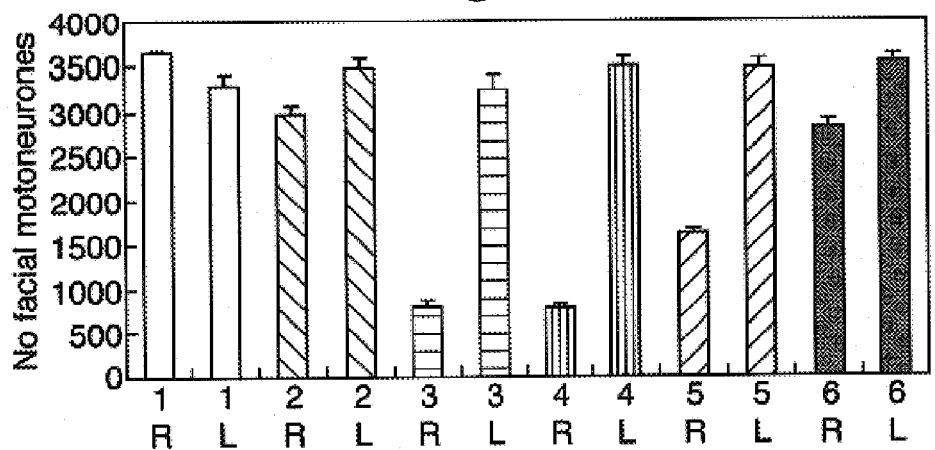
FIG. 1: Total numbers of motoneurones in the facial motor nucleus
KEY
1: normal
2: 1 month crush
3: 1 month avulsion
4: plasmid only—1 month avulsion
5: IGF-I plasmid—1 month avulsion
6: MGF plasmid—1 month avulsion
right: operated side; left: non-operated side

The present invention concerns the use of MGF in the treatment of neurological disorders, preferably motoneurone disorders.

MGF Polypeptides and Polynucleo Tides
Polypeptides

MGF stands for mechano-growth factor (cf. McKoy et al, 1999). As discussed above and explained in more detail in Chew et al (1995), Yang et al (1996) and McKoy et al (1999), MGF is an alternatively spliced variant of IGF-I. Liver-type IGF-I comprises amino acids encoded by exons 4 and 6 whereas MGF comprises amino acids encoded by exons 4, 5 and 6 MGF also has an altered reading frame at its carboxy terminus as a result of a 52 bp insert in exon 5, and is smaller because it is not glycosylated. Chew et al (1995) and Yang et al (1996) did not use the term MGF, but rather IGF-I Ec, to define the 4-5-6 splice variant. The muscle isoform that has the Ec domain is now known as MGF (cf McKoy et al, 1999). It is now clear that the particular form of the IGF-I Ec is produced by cardiac and skeletal muscle but only when they are subjected to mechanical activity.

Herein, MGF is understood to mean any IGF-I polypeptide having the 4-5-6 exon structure and the neurological properties identified by the Inventors, as discussed further below. The exon structure of MGF in human, rat and rabbit is illustrated in FIGS. 5, 6 and 7 (SEQ ID NOs 1/2, 3/4 and 5/6). For comparison, the exon structure of human, rat and rabbit L.IGF-I is given in FIGS. 8, 9 and 10 (SEQ ID NOs. 9/10, 11/12 and 13/14), and a comparison between MGP and L-IGF-I is made in FIG. 11.

Preferably, MGF of the invention will have the reading frame which, in native MGF, is generated by the 52 bp insert mentioned above. Preferably, MGF of the invention will not be glycosylated. However, it may be glycosylated or partially glycosylated in some embodiments. By partially glycosylated is meant up to 10, 20, 30, 50, 70, 80, 90, 95 or 99% as much glycosylation as L.IGF-I, e.g. containing some, but not all, of IGF-I's glycosylation sites. The pattern of glycosylation may be the same as that of L.IGF-I in terms of the type and placement of sugars or it may be different.

Preferably, MGF of the invention comprise exons 3, 4, 5 and 6 or equivalent sequences. Optionally, they may include exons 1 and/or 2, or equivalent sequences as well.

MGF of the invention may find its origins in any species that has 4-5-6 spliced IGF-I. Thus, MGF of the invention may have the sequence of human MGF, which is generally preferred. MGF having the sequence of an animal MGF may also be used, e.g. rat, rabbit, mouse, cow, sheep, goat, chicken, dog, cat MGF. Preferably, the species origin of the MGF used will be matched to the species of the subject to be treated. In particular, it is preferred to use human MGF to treat human patients.

The sequences of exons 3, 4, 5 and 6 human MGF (IGF-I-Ec) (SEQ ID NO. 1/2, FIG. 5), rat MGF (SEQ D NO 3/4, FIG. 6) and rabbit MGF (IGF-I Eb) (SEQ ID NO. 5/6, FIG. 7) are given below, together with their corresponding cDNA sequences. SEQ ID NOs. 1, 3 and 5 are the cDNAs; SEQ ID NOs. 2, 4 and 6 are the polypeptides. For comparison, the sequences of exons 3, 4 and 6 human (SEQ ID NO. 9/10, FIG. 8), rat (SEQ ID NO. 11/12, FIG. 9) and rabbit (SEQ ID NO. 13/14, FIG. 10) liver-type IGF-I (L.IGF-I) are also given (see FIG. 11 in particular for comparison). Polypeptides having the sequences of SEQ ID NOs. 2, 4 and 6 may be used in preferred embodiments of the invention.

Herein, MGF and functional equivalents thereof have the neurological properties identified by the Inventors. Thus, they have the capacity to effect motoneurone rescue. The exact degree of motoneurone rescue will vary from case to case, depending on which MGF is used and under what circumstances. However, with reference to the Examples, MGFs of the invention may be able to reduce motoneurone loss following nerve avulsion by up to 20, 30, 40, 50, 60, 70, 80, 90, 95, 99 or 100% in a treated subject compared to an equivalent situation in a non-treated subject. Reduction of motorneurone loss by 70% or more, or 80% more (i.e. to 30% or less or 20% or less) is preferred. The degree of rescue may be calculated using any suitable technique, e.g. a known technique such as Stereology (see the Examples). As a specific test, the techniques used in the Examples, which rely on measuring motoneurone rescue in response to facial nerve avulsion in rats, may be used. However it will be appreciated that this technique may not be ideal for assessing the properties of non-rat MGFs. Similar tests may thus be devised using other animal models. For example, tests relating to avulsion of other nerves may be devised. So far as human treatments are concerned, it will generally be necessary to rely on animal models so human MGF may have lower activity in these models than it has in vivo in humans.

MGFs having the sequence of naturally occurring MGFs are preferred. However, variant MGFs having the same basic 4-5-6 exon structure and neurological properties discussed herein may also be used.

Polypeptides of the invention may be encoded by polynucleotides as described below.

An MGF polypeptide of the invention may consist essentially of the amino acid sequence set out in SEQ ID NO. 2, 4 or 6 or a substantially homologous sequence, or of a fragment of either of these sequences, as long as the neurological properties of the invention are maintained. In general, the naturally occurring amino acid sequences shown in SEQ ID NOs. 2, 4 and 6 are preferred. However, the polypeptides of the invention include homologues of the natural sequences, and fragments of the natural sequences and of their homologues, which have the neurological properties of the invention.

In particular, a polypeptide of the invention may comprise:
(a) the polypeptide sequence of SEQ ID NO. 2 (human MGF), 4 (rat MGF), or 6 (rabbit MGF);
(b) a polypeptide sequence at least 70, 80, 90, 95, 98 or 99% homologous to, a polypeptide of (a);
(c) a sequence comprising the amino acids encoded wholly or party by exons 4, 5 and 6 of human, rat or rabbit MGF DNA of SEQ ID NO. 1, 3, or 5, or a sequence having 70% or greater homology thereto;
(d) a sequence encoded by a nucleic acid sequence capable of selectively hybridising to a sequence of (a), (b) or (c); or
(e) an allelic variant or species homologue of a sequence of (a).

Allelic Variants

An allelic variant will be a variant which occurs naturally and which will function in a substantially similar manner to the protein of SEQ ID NO. 2, 4 or 6 as defined above. Similarly, a species homologue of the protein will be the equivalent protein which occurs naturally in another species. Such a homologue may occur in any species, preferably a mammalian species, for example a bovine, equine, ovine, feline or canine species; such as cow, horse, sheep or goat, cat, or dog, or in a rodent species other than rat (SEQ ID NO. 4) or rabbit (SEQ ID NO. 6), or in a primate species other than human (SEQ ID NO. 2). Non-mammalian MGFs, for example piscine or avian MGFs, e.g. chicken MGF, are also MGFs of the invention. Within any one species, a homologue may exist as several allelic variants, and these will all be considered homologues of the protein of SEQ ID NO. 2, 4 or 6.

Allelic variants and species homologue can be obtained by methods known in the art, e.g. by probing suitable cell source with a probe derived from SEQ ID NO. 1, 3 or 5. Clones obtained can be manipulated by conventional techniques to generate a polypeptide of the invention which can be produced by recombinant or synthetic techniques known per se Homologues A polypeptide of the invention is preferably at least 70% homologous to the protein of SEQ ID NO. 2, 4 or 6 more preferably at least 80 or 90% and more preferably still at least 95, 97 or 99% homologous thereto over a region of at least 20, preferably at least 30, for instance at least 40, 60 or 100 or more contiguous amino acids, Methods of measuring protein homology are well known in the art and it will be understood by those of skill in the art that in the present context, homology is calculated on the basis of amino acid identity (sometimes referred to as "hard homology").

Degrees of homology can be measured by well-known methods, as discussed herein for polynucleotide sequences.

The sequence of the polypeptides of SEQ ED NOs. 2, 4 and 6 and of the allelic variants and species homologues can be modified to provide further polypeptides of the invention.

Substitutions

Amino acid substitutions may be made, for example from 1, 2 or 3 to 10, 20 or 30 substitutions. For example, a total of up to 1, 2, 5, 10 or 20 amino acids may be substituted over a length of 50, 100 or 200 amino acids in the polypeptides. For example, up to 20 amino acids substituted over any length of 50 amino acids. The modified polypeptide generally retains the neurological properties of the invention, as defined herein. Conservative substitutions may be made, for example according to the following table. Amino acids in the same block in the second column and preferably in the same line in the third column may be substituted for each other.

| ALIPHATIC | Non-polar | G A P |
| | | I L V |
| | Polar-uncharged | C S T M |
| | | N Q |
| | Polar-charged | D E |
| | | K R |
| AROMATIC | | H F W Y |

Fragments

Polypeptides of the invention also include fragments of the above-mentioned full length polypeptides and variants thereof, including fragments of the sequence set out in SEQ ID NOs. 2, 4 and 6. Such fragments typically retain the neurological properties of the invention.

Suitable fragments will generally be at least about 20, e.g. at least 20, 50 or 100 amino acids in size. Polypeptide fragments of the polypeptides of SEQ ID NOs. 2, 4 and 6 and allelic and species variants thereof may contain one or more (e.g. 2, 3, 5, 5 to 10 or more) substitutions, deletions or insertions, including conservative substitutions. Each substitution, insertion or deletion may be of any length, e.g. 1, 2, 3, 4, 5, 5 to 10 or 10 to 20 amino acids in length.

In particular, fragments of the invention may comprise the amino acids encoded by exons 4, 5 and 6 of human, rat or rabbit DNA of SEQ ID NO. 1, 3 or 5. The first amino aid of exon 4, Asn, is partly encoded by exon 3 (1 nucleotide) and partly by exon 4 (2 nucleotides). It is preferred that said first amino acid be present, in a fragment of the invention.

Chimeric Sequences

MGF polypeptides encoded by chimeric polypeptide sequences of the invention (see below) may be used.

Isolation, Purification and Modification

Polypeptides of the invention may be in a substantially isolated form. It will be understood that the polypeptide may be mixed with carriers or diluents which will not interfere with the intended purpose of the polypeptide and still be regarded as substantially isolated. A polypeptide of the invention may also be in a substantially purified form, in which case it will generally comprise the polypeptide in a preparation in which more than 70%, e.g. more than 80, 90, 95, 98 or 99% of the polypeptide in the preparation is a polypeptide of the invention.

Polypeptides of the invention may be provided in a form such that they are outside their natural cellular environment. Thus, they may be substantially isolated or purified, as discussed above, or in a cell which they do not occur in nature, e.g. a cell or other plant species, animals, yeast or bacteria.

Polypeptides of the invention may be modified for example by the addition of Histidine residues or a T7 tag to assist their identification or purification or by the addition of a signal sequence to promote their secretion from a cell.

A polypeptide of the invention may be labelled with a revealing label. The revealing label may be any suitable label which allows the polypeptide to be detected. Suitable labels include radioisotopes, e.g. $^{125}I$, $^{35}S$, enzymes, antibodies, polynucleotides and linkers such as biotin.

Polypeptides of the invention may be chemically modified, e.g. post-translationally modified. For example, they may comprise modified amino acid residues. They may also be glycosylated (see above), though MGF is not naturally glycosylated. Such modified polypeptides will be understood to be polypeptides of the invention.

Another possibility is to increase the stability, and hence half life of MGF in vivo by altering its sequence, e.g. to make it more amenable to glycosylation by introducing one or more glycosylation sites. Alternatively, modifications can be made that make MGF's primary amino acid structure more resistant to degradation.

The effects of modifications to MGF's sequence can be tested by any suitable method. For example, the binding properties and/or stability of variant MGFs can be tested by comparing them in vitro or in vivo to those of unmodified MGF.

Polynucleotides

Polynucleotides of the invention encode polypeptides of the invention.

Preferred polynucleotides of the invention comprise a coding sequence encoding a polypeptide having the neurological properties of the invention, which coding sequence is selected from:

(a) the coding sequence of any one of SEQ ID NO 1, 3 or 5;

(b) a sequence capable of selectively hybridising to a sequence of (a), or to a sequence complementary to a sequence of (a);

(c) a sequence having 70% or more homology to a sequence of (a);

(d) a sequence which is a fragment of the sequence of any one of (a) to (c); and (e) a sequence which differs from that of any one of (a) to (d) but which, owing to the degeneracy of the genetic code, encodes the same polypeptide.

Thus, the invention provides polynucleotides comprising the coding sequence as shown in any one of SEQ D NO. 1, 3 or 5 and variants thereof with related sequences Polynucleotides of the invention can be used to prepare vectors of the invention.

SEQ ID NOs. 1, 3 and 5

Preferred polynucleotides of the invention comprise coding sequences as shown in SEQ ID NOs. 1, 3 and 5.

Hybridisable Sequences A polynucleotide of the invention may hybridise selectively to coding sequence of SEQ ID NO. 1, 3 or 5 at a level significantly above background. Background hybridisation may occur, for example because of other cDNAs present in a cDNA library. The signal level generated by the interaction between a polynucleotide of the invention and the coding sequence of SEQ ID NO. 1, 3, 5, 7, 9 or 11 is typically at least 10 fold, preferably at least 100 fold, as intense as interactions between other polynucleotides and the coding sequence of SEQ ID NO. 1, 3 or 5. The intensity of interaction may be measured, for example by radiolabelling the probe, e.g. with $^{32}$P. Selective hybridisation is typically achieved using conditions of medium to high stringency (for example 0.03M sodium chloride and 0.03M sodium citrate at from about 50° C. to about 60° C., for example 45 to 50, 50 to 55 or 55 to 60° C., e.g. at 50 or 60° C.

However, such hybridisation may be carried out under any suitable conditions known in the art (see Sambrook et al, 1989, *Molecular cloning: A Laboratory Manual*). For example, if high stringency is required, suitable conditions include 0.2×SSX at around 60° C., for example 40 to 50° C., 50 to 60° C. or 60 to 70° C., e.g. at 50 or 60° C. If lower stringency is required, suitable conditions include 2×SSC at around 60° C., for example 40 to 50° C., 50 to 60° C. or 60 to 70° C., e.g. at 50 or 60° C.

Stringency typically occurs in a range from about Tm−5° C. (5° C. below the melt temperature (Tm) of the two sequences hybridising to each other in a duplex) to about 20° C. to 25° C. below Tm. Thus, according to the invention, a hybridisable sequence may be one which hybridises to SEQ ID NO. 1, 3 or 5 at a temperature of from Tm to Tm−25° C., e.g. Tm to Tm−5° C., Tm−5 to Tm−10° C., Tm−10 to Tm−20° C. or Tm−20 to Tm−25° C.

Homologous Sequences

A polynucleotide sequence of the invention, will comprise a coding sequence at least 70% preferably at least 80 or 90% and more preferably at least 95, 98 or 99%, homologous to the coding sequence of SEQ ID NO. 1, 3 or 5.

Such homology will preferably apply over a region of at least 20, preferably at least 50, for instance 100 to 500 or more, contiguous nucleotides.

Methods of measuring nucleic acid and polypeptides homology are well known in the art. These methods can be applied to measurement of homology for both polypeptides and nucleic acids of the invention. For example, the UWGCG Package provides the BESTFIT program which can be used to calculate homology (Devereux et al, 1984, *Nucleic Acids Research* 12, p. 387–395).

Similarly, the PILEUP and BLAST algorithms can be used to line up sequences (for example as described in Altschul, S. F., 1993, *J. Mol. Evol.* 30:290–300; Altschul, S. F. et al, 1990) *J. Mol. Biol.* 215:403–410).

Many different settings are possible for such programs. According to the invention, the default settings may be used.

In more detail, the BLAST algorithm is suitable for determining sequence similarity and it is described in Altschul et al (1990) J. Mol. Biol. 215:403–410. Software for performing BLAST analyses is publicly available through the National Center for Biotechnology Information (internet address nih/nlm.hih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighborhood word score threshold (Altschul et al, supra). These initial neighborhood word hits act as seeds for initiating searches to find HSPs containing them. The word hits are extended in both directions along each sequence for as far as the cumulative alignment score can be increased. Extensions for the word hits in ch direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) Proc. Natl. Acad. Sci. USA 89:10915–10919) alignments (B) of 50, expectation (E) of 10, M=5, N=4, and a comparison of both strands.

The BLAST algorithm performs a statistical analysis of the similarity between two sequences; see e.g. Karlin and Altschul (1993) *Proc. Natl. Sci.* USA 90:5873–5787. One measure of similarity provided by the BLAST algorithm is the smallest sum probability (P(N)), which provides an indication of the probability by which a match between two nucleotide or amino acid sequences would occur by chance. For example, a nucleic acid is considered similar to a fused gene or cDNA if the smallest sum probability in comparison of the test nucleic acid to a fused nucleic acid is less than about 1, preferably less than about 0.1, more preferably less than about 0.01, and most preferably less than about 0.001.

Fragments

Also included within the scope of the invention are sequences which are fragments of the sequences of (a) to (c) above but have the neurological properties of the invention.

In particular, fragments may comprise exons 4, 5 and 6 of human, rat or rabbit MGF DNA of SEQ ID NO. 1, 3 or 5

The first amino acid of exon 4, Asn, is partly encoded by exon 3 and partly by exon 4. It is preferred that the necessary coding bases from exon 3 are present to encode said first amino acid, Asn.

Degenerate Sequences

Also included within the scope of the invention are sequences that differ from those of (a) to (d) but which, because of the degeneracy of the genetic code, encode the same protective polypeptides. For example, the invention provides degenerate variants of the sequence of SEQ ID NOs. 1, 3 and 5 that also encode the polypeptide of SEQ ID NOs. 2, 4 and 6.

Complementary Sequences

In addition, the invention provides polynucleotides having sequences complementary to any of the above-mentioned sequences.

Chimeric Sequences

Chimeric sequences comprising exons from more than one species may also be used. For example, one or more of exons 3 to 6 may be derived from human and one or more from rat and/or rabbit.

Further Properties

The nucleic sequences of the invention may be of any length as long as they encode a polypeptide of the invention. A nucleic acid sequence according to the invention may be a contiguous fragment of the sequence of SEQ ID NO. 1, 3 or 5 or a sequence that is related to it in any of the ways described above. Alternatively, nucleic acids of the invention may comprise DNA sequences that are not contiguous in the sequence of SEQ ID NO. 1, 3 or 5. These sequences may be fragments of the sequence of SEQ ID NO. 1, 3 or 5 or nucleic acid sequences that are related to such fragments in any of the ways described above. Nucleic acid sequences of the invention will preferably comprise at least 50 bases or base pairs, for example 50 to 100, 100 to 500, 500 to 1000 or 1000 to 2000 bases or base pairs.

Any combination of the above-mentioned degrees of homology and minimum sizes may be used to defined polynucleotides of the invention, with the more stringent combinations (e.g. higher homology over longer lengths and/or hybridisation under more stringent conditions) being preferred. Thus, for example a polynucleotide which is at least 90% homologous over 100, preferably over 200 nucleotides forms one aspect of the invention, as does a polynucleotide which is at least 95% homologous over 100 or 200 nucleotides.

Polynucleotides of the invention may comprise DNA or RNA. They may also be polynucleotides which include within them synthetic or modified nucleotides. A number of different types of modification to polynucleotides are known in the art. Modifications may, for example enhance resistance to nucleases and/or enhance ability to enter cells. For example, phosphorothioate oligonucleotides may be used. Other deoxynucleotide analogs include methylphosphonates, phosphoramidates, phosphorodithioates, N3'P5'-phosphoramidates and oligoribonucleotide phosphorothioates and their 2'-O-alkyl analogs and 2'-O-methyliribonucleotide methylphosphonates. A further possible modification is the addition of acridine or polylysine chains at the 3' and/or 5' ends of the molecule.

Alternatively mixed backbone oligonucleotides (MBOs) may be used. MBOs contain segments of phosphothioate oligodeoxynucleotides and appropriately placed segments of modified oligodeoxy- or oligoribonucleotides. MBOs have segments of phosphorothioate linkages and other segments of other modified oligonucleotides, such as methylphosphonate, which is non-ionic, and very resistant to nucleases or 2'-O-alkyloliogoribonucleotides. For the purposes of the present invention, it is to be understood that the polynucleotides described herein may be modified by any method available in the art. Such modifications may be carried out in order to enhance the in vivo activity or lifespan of polynucleotides of the invention.

Polynucleotides of the invention may be used to produce a primer, e.g. a PCR primer, a primer for an alternative amplification reaction, a probe, e.g. labelled with a revealing label by conventional means using radioactive or non-radioactive labels, or the polynucleotides may be cloned into vectors. Such primers, probes and other fragments will preferably be at least 10, preferably at least 15 or 20, for example at least 25, 30 or 40 nucleotides in length. These will be useful in identifying species homologues and allelic variants as discussed above.

Polynucleotides such as a DNA polynucleotides and primers according to the invention may be produced recombinantly, synthetically, or by any means available to those of skill in the art. They may also be cloned by standard techniques. The polynucleotides are typically provided in isolated and/or purified form.

In general, primers will be produced by synthetic means, involving a stepwise manufacture of the desired nucleic acid sequence one nucleotide at a time. Techniques for accomplishing this using automated techniques are readily available in the art Genomic clones corresponding to the cDNAs of SEQ ID NOs. 1, 3 and 5 containing, for example introns and promoter regions are also aspects of the invention and may also be produced using recombinant means, for example using PCR (polymerase chain reaction) cloning techniques.

The 4-5-6 exon pattern of MGF is characteristic of polynucleotides of the invention. Any suitable method may be used to ensure that this pattern is reflected in the coding sequence, and thus in the encoded polypeptide. For example, cDNA sequences lacking introns and splice signals and including the coding sequences of exons 4, 5 and 6 may be used. Alternatively, genomic DNA may be used if it will be correctly spliced in the situation at hand.

Although in general the techniques mentioned herein are well known in the art, reference may be made in particular to Sambrook et al (1989), *Molecular Cloning. A Laboratory Manual*.

Polynucleotides which are not 100% homologous to the sequences of the present invention but fall within the scope of the invention, as described above, can be obtained in a number of ways, for example by probing cDNA or genomic libraries from other plant species with probes derived from SEQ ID NO. 1, 3 or 5. Degenerate probes can be prepared by means known in the art to take into account the possibility of degenerate variation between the DNA sequences of SEQ ID NO 1, 3 or 5 and the sequences being probed for under conditions of medium to high stringency (for example 0.03M sodium chloride and 0.03M sodium citrate at from about 50° C. to about 60° C.), or other suitable conditions (e.g. as described above)

Allelic variants and species homologues may also be obtained using degenerate PCR which will use primers designed to target sequences within the variants and homologues encoding likely conserved amino acid sequences. Likely conserved sequences can be predicted from aligning the amino acid sequences of the invention (SEQ ID NO 2, 4 or 6) with each other and/or with those of any homologous sequences known in the art. The primers will contain one or more degenerate positions and will be used at stringency conditions lower than those used for cloning sequences with single sequence primers against known sequences.

Alternatively, such polynucleotides may be obtained by site-directed mutagenesis of sequences of SEQ ID NO. 1, 3 or 5 or allelic variants thereof. This may be useful where, for example silent codon changes are required to sequences to optimise codon preferences for a particular host cell in which the polynucleotide sequences are being expressed. Other sequences may be desired in order to introduce restriction enzyme recognition sites, or to alter the properties or function of the polypeptides encoded by the polynucleotides.

The invention further provides double stranded polynucleotides comprising a polynucleotide of the invention and its complement.

Polynucleotides, probes or primers of the invention may carry a revealing label. Suitable labels include radiosotopes such as $^{32}P$ or $^{35}S$, enzyme labels, or other protein labels such as biotin. Such labels may be added to polynucleotides, probes or primers of the invention and may be detected using techniques known per se.

Production of Polypeptides

Polypeptides of the invention may be produced in any suitable manner. In some embodiments they may be extracted from animal tissues However, it is preferred that they be produced recombinantly from polynucleotides of the invention. This can be done using known techniques.

Repair of Nerve Damage

Localisation of MGF at the Site of the Nerve Damage

MGF may be localised at the site of the nerve damage by any suitable means. For example, it can be localised at the damage site within a matrix, e.g. a gel or solid.

Preferably, MGF is localised at the damage site by means of a conduit around the nerve at the damage site. This is especially preferred where it is desired to bridge a gap in a severed nerve. However, other approaches may be better where the nerve is not severed, but rather damaged or degenerating. One example of such a condition is neuropraxia.

Conduits

A conduit may be placed around the nerve damage site. The presence of the conduit per se may encourage nerve damage repair but the localisation of MGF by the conduit will enhance this.

The conduit may be composed of any suitable material. For example, it may be composed of a non-bioabsorbable material such as silicone, which has been widely used in the past.

However, bioabsorbable materials are preferred, as they can be absorbed by the body when the damage is repaired. Collagen conduits (available from Integra Life Sciences) are one option in this respect.

In general, flexibility and low inflammatory response are desirable characteristics of conduits of the invention.

Conduits comprising, or composed of, PHB elicit only low inflammatory (macrophage) response. They are also known to have positive effect on nerve regeneration independent of MGF (see above) so a combined treatment will be particularly effective.

PHB is a bacterial product and occurs in granular form in the bacterial cytoplasm. Preferably, PHB of bacterial origin will be used, though PHB from other sources can also be used in appropriate. PHB can be formed into bioabsorbable sheets and such sheets are preferably used to form the conduits of the invention.

Conduits, especially PHB conduits, may be formed and put in place by any known method. The methods of Hazari et al, 1999 (Supra) are preferred.

In particular, conduits are normally formed from PHB sheets cut so that the orientation of PHB fibres is along the length of the nerve. This promotes nerve damage repair by contact guidance.

A conduit is then formed by rolling the sheet around an object of suitable diameter, e.g. a 16 G intravenous cannula, thus standardising the internal diameter of the coagulate. A 16 G intravenous cannula gives an internal diameter of 1.6 mm. However, other internal diameters can be achieved by rolling around different template objects. A person of skill in the art will be able to select the correct size for the situation concerned. The rolled sheets are then sealed longitudely. Preferably, an adhesive is used, e.g. a cyano-acrylate glue (for example, histoacryl®, Braun Melsungen AG, Melsungen, Germany). Then, the conduit, preferably still rolled around the template object, is typically presoaked in saline to saturate the polymer and ensure maximum expansion of the fibres without a reduction in the internal diameter of the conduit. The skilled person will be able to determine a suitable size for the conduit based on the nerve damage to be repaired. However, a conduit will typically be formed from a rectangular sheet of PHB cut from a larger sheet. A person of skill in the art will be able to select the correct size for the situation concerned.

As discussed above, a conduit will be typically formed from a rolled sheet. However, conduits can also be manufactured as pre-formed tubes.

The conduits can be put in place by any means known in the art for example by the surgical techniques discussed in Hazari et al, Typically, a conduit will be used to bridge the severed ends of the nerve by entubulating both ends of the nerve within the conduit and securing with sutures to the epineurium. The length of the conduit will be chosen according to the length of the gap. A person skilled in the art will be able to select the correct size for the situation concerned. Typically, a short segment of each nerve stamp will be entubulated.

In a preferred embodiment, the conduits of the invention are used to repair nerve damage that involves severing of the nerve.

Preferably, the nerves to which damage is to be repaired are peripheral nerves, e.g. nerves in the arms or legs.

MGF according to the invention may be introduced into the conduit of the invention by any suitable means. For example, it may be coated on the inside of the conduit, impregnated into the conduit, e.g. during the saline soaking step mentioned above, provided in a matrix, e.g. a gel matrix within the conduit or around the outside the conduit; alternatively, it may be delivered to the conduit in situ, e.g. by injection The protein may be attached to the conduit by any suitable means.

Preventing Target Organ Degeneration

When a nerve that innervates an organ (a "target" organ) is damaged, especially severed, the organ may degenerate because of the absence of innervation. Therefore, localisation of MGF around the nerve damage site is preferably performed in combination with a treatment that prevents or diminishes target organ degeneration. Any suitable treatment known in the art way be used In particular, where the target organ is a muscle, MGF can be used to prevent apoptosis of the muscle cells and thus prevent or diminish degeneration. MGF or an MGF-encoding nucleic acid can be delivered in any suitable way to achieve this. In particular, an MGF encoding nucleic acid can be introduced by intramuscular injection and expressed in situ to generate MGF. Other growth factors can also be used as appropriate.

Other neurotrophic factors, including glial cell-derived neurotrophic factor, brain-derived neurotrophic factor, neurotrophin-3 and neurotrophin 4/5, may also be used, as they are found in skeletal muscle and other target organs, and they promote the survival of a variety of neurone types including motoneurones (e.g. Bock G. R. & Goode, 1996, Growth factors as drugs for neurological and sensory disorders. Ciba Foundation Symposium 196. New York: John Wiley & Sons).

Pharmaceutical Formulations for Nerve Damage Repair

The polypeptides and nucleic acids of the invention are preferably delivered in the form of a pharmaceutical formulation comprising a pharmaceutically acceptable carrier or diluent. Any suitable pharmaceutical formulation may be used.

For example, suitable formulations may include aqueous and non-aqueous sterile injection solutions which may contain anti-oxidants, buffers, bacteriostats, bactericidal antibiotics and solutes which render the formulation isotonic with the bodily fluids of the intended recipient; and aqueous and non-aqueous sterile suspensions which may include suspending agents and thickening agents. The formulations may be presented in unit-dose or multi-dose containers. For example, sealed ampoules and vials, and may be stored in a frozen or freeze-dried (lyophilized) condition requiring only the addition of the sterile liquid carrier, for example water for injections, immediately prior to use.

In particular, formulations that encourage localisation of MGF at the site of nerve damage are preferred, for example gels and suspensions that discourage the active ingredient from moving away from the site.

Owing to MGF's short half-life, slow-release or delivery agents may be used. Any suitable pharmaceutical formulation may be used to effect slow-release of MGF of the invention. Liposome formulations are one possibility.

In particular, a slow release "toothpaste-type" matrix is preferred. This can be coated on to the inside of a conduit of the invention. A similar formulation, extruded from a syringe, could be used to combat degeneration of target organs, especially muscles whilst nerve damage is repaired.

It should be understood that in addition to the ingredients particularly mentioned above the formulations of this invention may include other agents conventional in the art having regard to the type of formulation in question. Sterile, pyrogen-free aqueous and non-aqueous solutions are preferred.

Dosages for Nerve Damage Repair

The proteins, nucleic acids and vectors of the invention may be delivered in any suitable dosage, and using any suitable dosage regime Persons of skill in the art will appreciate that the dosage amount and regime may be adapted to ensure optimal treatment of the particular condition to be treated, depending on numerous factors. Some such factors may be the age, sex and clinical condition of the subject to be treated and of course the type and severity of nerve damage concerned.

As a guideline, amounts of MGF in the region of from 1 to 1000 mg, from 10 to 100 mg and 100 to 500 mg or from 500 to 1000 mg may be localised around the site of the nerve damage.

Dosage schedules will also vary according to the condition to be treated. Typically, however, all of the MGF necessary will be administered at the outset of the procedure so that the surgical insertion can be closed. As discussed above, slow release formulations may be used to ensure delivery over a period of time at the nerve damage site. This is particularly desirable in view of MGF's short half-life.

Combinations of MGF and Other Neurotrophic Factors in Nerve Damage Repair

MGF polypeptides and nucleic acids of the invention can be administered in combination with other neurologically active agents. This may be either to enhance repair of nerve damage or to prevent or diminish target organ degeneration or both. Any additional neurological active agent may be used in this way. Such agents may be non-polypeptide molecules or they may be polypeptides. If they are polypeptides, they may be delivered as polypeptides or as nucleic acids encoding such polypeptides. This may be done by any suitable method known in the art.

Polypeptide growth factors having neurological activity are preferred. For example, neurotophins such as Brain-Derived Neurotrophic Factor (BDNF), Neurotrophin-3 (NT-3), NT-4, NT-5 or Nerve Growth Factor (NGF) may be used. Similarly, neurologically active cytokines such as Ciliary Neurotrophic factor (CNTF) can be used. Similarly, neurologically active transcription factors such as Brn 3a, Brn 3b and Brn 3c may be used.

When an MGF of the invention is combined with another neurologically active agent in the treatment of a neurological disorder the two may be combined in the same pharmaceutical composition. Alternatively, they may be administered in separate compositions. They may be administered simultaneously, separately or sequentially and at the same site or a different site. For example, MGF may be present within a conduit of the invention that joins the two ends of a severed nerve, and another growth factor may be administered either within the conduit to assist MGF's nerve repair more action, and/or outside the conduit, or generally to the target organ to stop its degeneration whilst the nerve is repaired.

EXAMPLES

Introduction

In this study, we have used a model of axotomy-induced motoneuronal degeneration in adult rats to examine the protective effects of two isoforms of insulin-like growth factor-I (IGF-I): the commonly-used liver-type isoform (L.IGF-I) and a newly-identified splice variant of IGF-I which is produced by active muscle (Yang et al, 1996) and which we have termed "mechano growth factor" (MGF). Our analysis of the structure of MGF indicates that it probably has different tissue binding and a shorter half-life than L.IGF-I making it particularly suited to mediating such local interactions in a paracrine/autocrine manner To enable the local action of L.IGF-I and MGF at the neuromuscular junction and avoid the need for repeated injections of these short half-life molecules, we used a plasmid DNA vector to deliver the genes for these growth factors to muscles.

Methods

Three 20 $\mu$l equidistant injections were made into the right whisker pad of lightly-anaesthetised (2% halothane) 6m Sprague-Dawley rats (n=4 per group). In the first group (plasmid), 1.5 $\mu$g/$\mu$l plasmid DNA containing the rat MGF gene was injected and in the third group 0.65 $\mu$g/$\mu$l plasmid DNA containing the rat MGF gene was injected. After 7 days, the right facial nerve was avulsed as it emerged from the stylomastoid foramen using gentle traction. In other groups, the right facial nerve was crushed (n=4) or avulsed (n=4) without prior intramuscular injection of plasmid. After 1 month, all rats, including 4 non-operated rats, were anaesthetised then perfused with 4% paraformaldehyde and the region of the brainstem containing the facial nucleus sectioned serially at 70 $\mu$m using a vibratome. Every $5^{th}$ section was taken in a systematic random manner and stained with the fluorescent dye YOYO (1:1000, molecular probes) for estimation of total facial motoneurone number using a modification of the discetor method for use in the confocal microscope (Johnson et al, 1998). Briefly, 2 optical sections separated by 10 $\mu$m were taken through the 70 $\mu$m vibratome slice, one image was stored as shades of green and the other as shades of red. The two optical sections were then merged on screen and only those neurones which were present in one optical section but not the other (which in this case were green, but not red or shades of yellow) were counted. After determining the volume of the facial nucleus using stereology (West M. J. Trends in Neuroscience 1999. 22: 51–61) the total number of facial motoneurones was then calculated.

Results

Figure 2A:
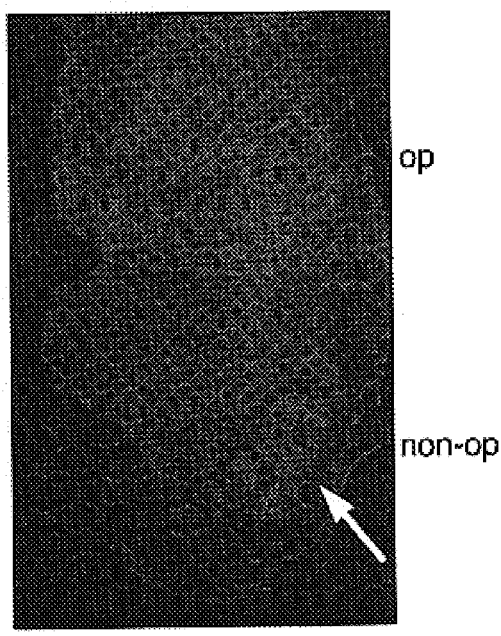
FIG. 2: Avulsion (control experiments)
(a) Low magnification view of a transverse section through the brainstem at the level of the facial nucleus, 1 month following facial nerve avulsion. Numbers of motoneurones in the facial nucleus of the operated side (b) are markedly reduced compared to the non-operated nucleus (arrow and inset c). 70 $\mu$m vibratome section stained with YOYO and viewed using epifluorescence.
Figure 2B:
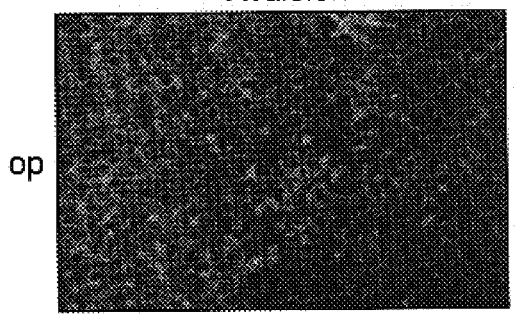
Figure 2C:
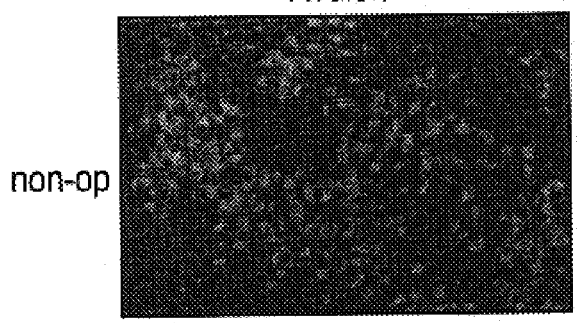
Figure 3A:
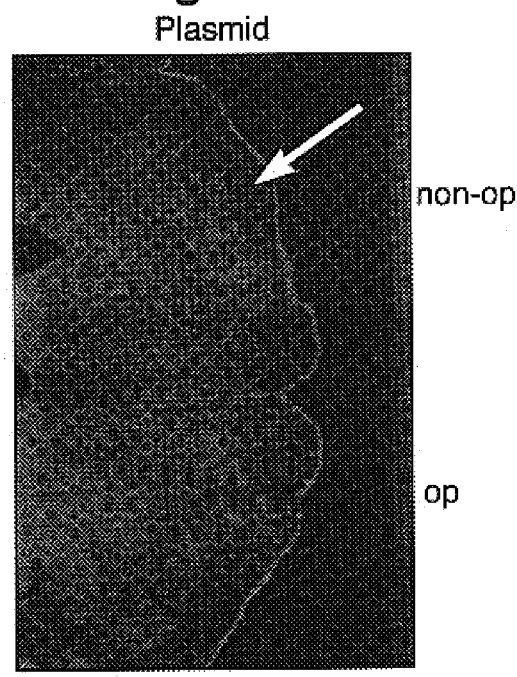
FIG. 3: Plasmid experiments
(a) Low magnification view of the brainstem at the level of the facial nucleus Plasmid DNA without any gene insert was injected into the right snout muscle. 7 days later the right facial nerve was avulsed and the animal allowed to survive for 1 month. Like the effect of avulsion only (FIG. 1), numbers of motoneurones in the facial nucleus of the operated side (c) are markedly reduced compared to the non-operated nucleus (arrow and inset b) 70 $\mu$m vibratome section stained with YOYO and viewed using epiflourescence.
Figure 3B:
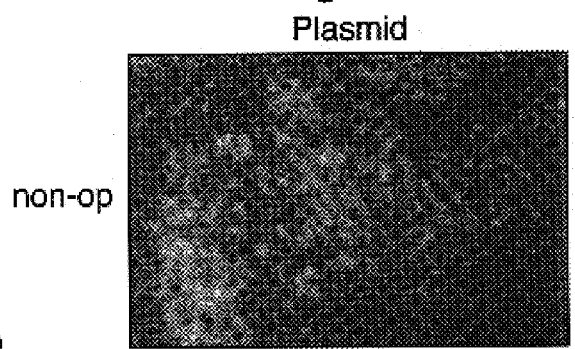
Figure 3C:
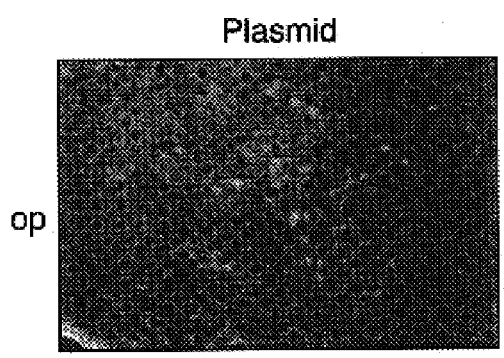
Figure 4A:
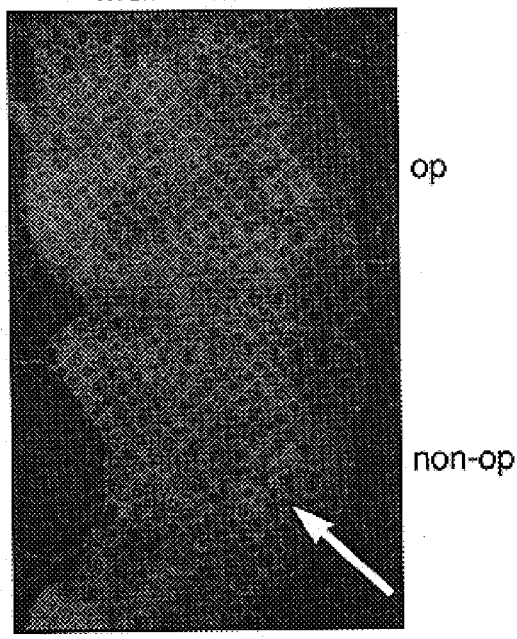
FIG. 4: MGF plasmid experiments
(a) Low magnification view of the brainstem at the level of the facial nucleus. Plasmid DNA containing the rat MGF gene was injected into the right snout muscle. 7 days later the right facial nerve was avulsed and the animal allowed to survive for 1 month Numbers of motoneurones in the facial nucleus of the operated side (b) are similar to the non-operated nucleus (arrow and inset c). 70 $\mu$m vibratome section stained with YOYO and viewed using epiflourescence.
Figure 4B:
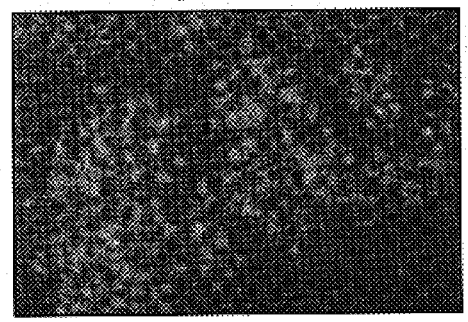
Figure 4C:
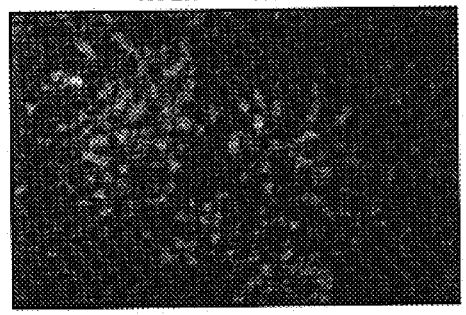
Figure 12:
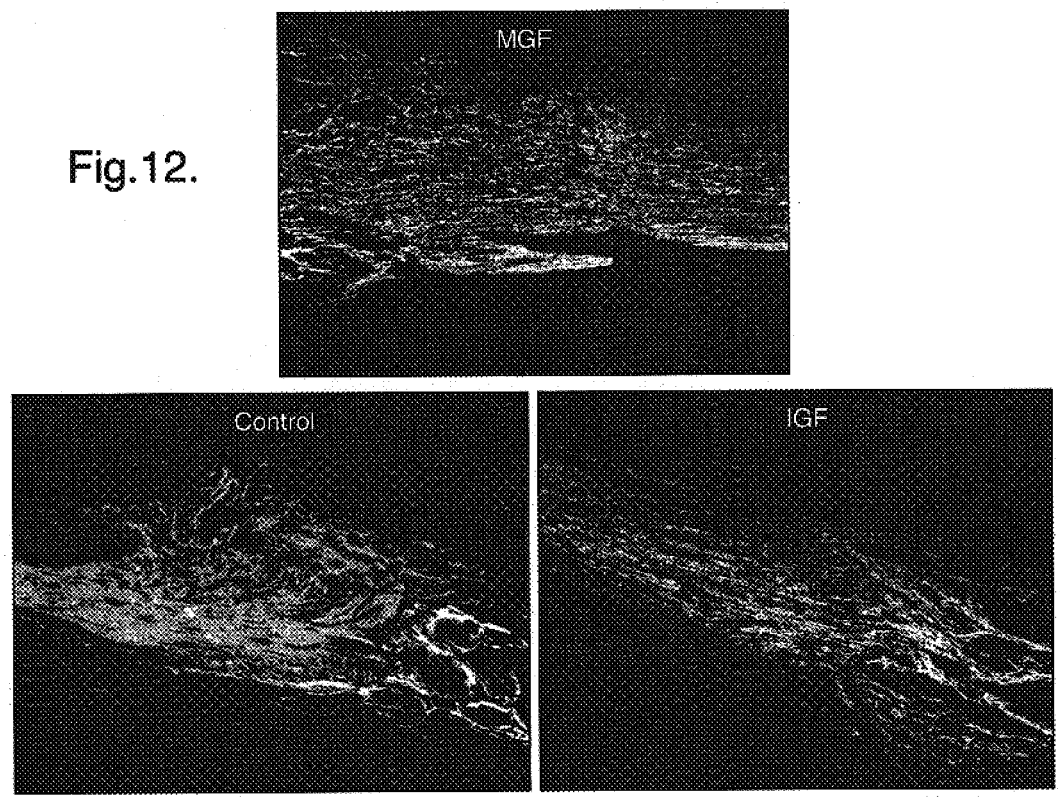
FIG. 12. Staining for axon (Pan NF, in red in original colour) and supporting Schwann cells (S100, in green in original colour) showing axonal regeneration in the three experimental groups. The axon regrowth in the MGF group is more abundant and reaches further into the distal nerve than the axons in the other two experimental groups. Top centre; MGF, lower left; control with "empty" vector, lower right: L.IGF.

The normal adult rat facial nucleus contains approximately 3,500 motoneurones (Table 1, FIG. 1). 1 month following nerve crush, approximately 15% of the motoneurones are lost ipsilaterally (p<0.05, Mann Whitney U test), while 1 month following nerve avulsion approximately 75% of the motoneurones are lost FIG. 2). Injection of plasmid DNA alone into the snout 7 days before avulsion had no effect on the massive motoneuronal loss seen 1 month later (FIG. 3). However, prior intramuscular injection of the plasmid containing the gene for L.IGF-I reduced the motoneuronal loss 1 month following avulsion to 53% and injection of the plasmid containing the MGF gene reduced motoneuronal loss 1 month following avulsion to 21% (FIG. 4).

TABLE 1

Total numbers of motoneurones in the facial motor nucleus 1 month following nerve avulsion (a simple tug to damage the nerve) with or without prior intramuscular gene transfer

|  | No avulsion | | Crush | | Avulsion | | Control plasmid-avulsion | | IGF-avulsion | | MGF-avulsion | |
| --- | --- | --- | --- | --- | --- | --- | --- | --- | --- | --- | --- | --- |
|  | right | left | right | left | right | left | right | left | right | left | right | left |
| rat 1 | 3676 | 3404 | 3014 | 3619 | 884 | 3323 | 750 | 3384 | 1699 | 3386 | 2674 | 3624 |
| rat 2 | 3622 | 3118 | 2889 | 3404 | 889 | 3372 | 798 | 3488 | 1556 | 3413 | 2934 | 3582 |
| rat 3 | 3631 | 3385 | 2903 | 3314 | 719 | 3397 | 819 | 3631 | 1660 | 3438 | 2800 | 3561 |
| rat 4 | 3666 | 3233 | 3083 | 3523 | 733 | 3023 | 869 | 3606 | 1640 | 3655 | 2823 | 3429 |
| mean | 3648.7 | 3285 | 2972.3 | 3465 | 806.3 | 3278.8 | 809 | 3527.3 | 1638.8 | 3473 | 2807.8 | 3549 |
| sd | 22.8 | 116.9 | 80.2 | 115.8 | 80.4 | 150.0 | 42.7 | 98.8 | 52.3 | 106.7 | 92.4 | 72.9 |

Example 2

Sciatic Nerve Repair Using IGF Isoforms in Conjunction with PHB Conduits

The aim was to assess whether local administration of MGF to an injured nerve improves the axonal regrowth in the acute phase of the regeneration process. MGF was administered as cDNA embedded in hydrogel matrix, inserted in a bioresorbable polymer conduit. The advantage of this approach is that the growth factor is immediately available to the injured neurons, and that the protected microenvironment created by the bioengineered construct would facilitate nerve fibres regrowth.

Poly-3-hydroxybutyrate (PHB) was the polymer of choice, as it is of natural origin, non-antigenic and can be manufactured in sheets composed of fibres with unidirectional orientation. In previous experiments, PHB conduits have been shown to promote regeneration in nerve gaps up to 4 cm in length. The addition of alginate hydrogel also allowed the suspension of engineered MGF gene for the gene product ready to be taken up by retrograde transport delivery to the neuronal cell bodies in spinal cord and dorsal root ganglia.

At two weeks post-operatively, the rats were killed, the repaired nerve harvested in its entirety and fixed in Zamboni solution overnight at +4° C. Following extensive washes in PBS solution, the tissue was blocked for cryostat sectioning. Tissue sections were processed for immunohistochemistry using primary antibodies to S100 (a marker for Schwann cells) and PanNF (a pan-neuronal marker). The staining was carried out according to the indirect immunofluorescence method using both primary antibodies on the same section, in order to obtain a double staining for the two markers. This facilitates the comparison of the staining and allows precise morphological localisation of the regrowing axons and glial cells. The sections were coded, and the examiner was blind to the groups to which the section under examination belonged.

Nerve regeneration was observed in samples from all groups In particular, a continuous cord of Schwann cells was seen to extend between proximal and distal nerve ends, showing similar quantities for MGF, IGFI and control groups. These results indicate that the conduit or the matrix used in these experiments did not impede regeneration. When axonal regeneration was examined, the results were very different from those seen with Schwann cells staining. Indeed, axonal regeneration was scarce in the conduits filled with alginateand control plasmid (i.e. no cDNA insert), with few axons extending into the distal nerve stump. Addition of IFGI cDNA-plasmid produced an increased amount of axonal regeneration, with a moderate number of fibres reaching into the distal nerve stump. Regeneration was further enchanced when MGF cDNA-plasmid was added to the alginate matrix. In these conduits, a vigorous regeneration was seen throughout the width of the nerve, with numerous axons extending well into the distal nerve stump. No quantification was attempted, but the disparity of the staining was so considerable as to be able to determine without difficulties the difference between groups

REFERENCES

Chew et at, *Endocrinology* 136, No. 5 (1995)
Eisen et al, *"Amyotrophic Lateral Sclerosis"* (Cambridge University Press, Cambridge, 1998)
Hazari et al, *British J. Plastic Surgery* 52, 653–57 (1999)
Goldspink et al, *J. Physiol.* 4968, 1628 (1996)
Jansen et al, *Mol. Cell Endocrinology* 78: 115–25 (1991)
Johnson et al, *Neuroscience* 84: 141–150 (1998)
Layall, *"Transcriptional regulation of the ovine IGF-1 Gene"*, PhD Thesis, University of Cambridge (1996)
Lundborg et al, *J. Hand Surgery* 22; 99–106 (1997)
Manes et al, *Endocrinology* 138; 905–915 (1997)
McKoy et al, *J. Physiol.* 516.2, 583–592 (1999)
Rotwein et al, *J. Biol. Chem.* 261:4828–3 (1986)
Skarli et al, *J. Physiol.* 509.8, 192.8 (1998)
Tobin et al, *Mol. Endocrinology* 1914–20(1990)
Vejsada et al, *Eur. J. Neurosci.* 7: 108–115 (1995)
Vesjada et al, *Neuroscience* 84: 129–139 (1998)
Yang et al, *Journal of muscle cell research and cell motility* 4: 487–496 (1996)

---

What is claimed is:

1. A method of treating a damaged nerve of the peripheral nervous system, said treatment comprising administering to a subject comprising said nerve an effective non-toxic amount of an MGF (mechano-growth factor) polypeptide having the ability to reduce motoneurone loss by 20% or greater in response to nerve avulsion, said administration comprising delivering said MGF polypeptide to the site of said damage;

said MGF polypeptide comprising at least one sequence selected from the group consisting of:

(a) an amino acid sequence comprising a sequence encoded by exons 3-4-5-6 of a mammalian MGF; and (b) an amino acid sequence having 80% or greater sequence identity, over the sequence encoded by exons 3-4-5-6, to an amino acid sequence of (a).

2. A method of claim 1 wherein said MGF polypeptide is administered to said subject at a site of said damaged nerve by means of a conduit placed around the damaged nerve.

3. A method of claim 2 wherein the conduit comprises Poly-3-hydroxy-butyrate (PHB).

4. A method of claim 2 wherein said conduit comprises at least one of collagen and silicone.

5. A method of claim 2 wherein the damaged nerve was severed.

6. A method of claim 1 wherein the damaged nerve was severed.

7. A method of claim 1 wherein said MGF polypeptide has the ability to reduce motoneurone loss by 50% or greater in response to nerve avulsion.

8. A method of claim 1 wherein said MGF polypeptide has the ability to reduce motoneurone loss by 80% or greater in response to nerve avulsion.

9. A method of claim 1 wherein the MGF polypeptide is unglycosylated.

10. A method of claim 1 wherein said MGF polypeptide comprises an amino acid sequence selected from the group consisting of SEQ ID NOs: 2, 4 and 6.

11. A method of claim 1 wherein said MGF polypeptide comprises an amino acid sequence having 90% or greater sequence identity, over the sequence encoded by exons 3-4-5-6, to an amino acid sequence of (a).

12. A method of claim 1 wherein said MGF polypeptide comprises an amino acid sequence of 80% or greater identity to an amino acid sequence selected from the group consisting of SEQ ID NOs: 2, 4, and 6.

13. A method of treating a damaged nerve of the peripheral nervous system, said treatment comprising administering to a subject comprising said nerve an effective non-toxic amount of an MGF (mechano-growth factor) polypeptide having the ability to reduce motoneurone loss by 20% or greater in response to nerve avulsion, said administration comprising delivering said MGF polypeptide to the site of said damage;

said MGF polypeptide comprising at least one sequence selected from the group consisting of:

(a) an amino acid sequence comprising a sequence encoded by exons 4-5-6 of a mammalian MGF; and (b) an amino acid sequence having 80% or greater sequence identity, over the sequence encoded by exons 4-5-6, to an amino acid sequence of (a).

14. A method of claim 13 wherein said MGF polypeptide is administered to said subject at a site of said damaged nerve by means of a conduit placed around the damaged nerve.

15. A method of claim 14 wherein the conduit comprises Poly-3-hydroxy-butyrate (PHB).

16. A method of claim 14 wherein said conduit comprises at least one of collagen and silicone.

17. A method of claim 14 wherein the damaged nerve was severed.

18. A method of claim 13 wherein the damaged nerve was severed.

19. A method of claim 13 wherein the MGF polypeptide is unglycosylated.

20. A method of claim 13 wherein said MGF polypeptide comprises an amino acid so sequence selected from the group consisting of amino acids 26–110 of SEQ ID NO:2, amino acids 26–111 of SEQ ID NO:4, and amino acids 26–111 of SEQ ID NO:6.

21. A method of claim 13 wherein said MGF polypeptide comprises an amino acid sequence which has 90% or greater sequence identity, over the sequence encoded by exons 4-5-6, with a sequence of (a).

22. A method of claim 13 wherein said MGP polypeptide comprises an amino acid sequence which has 80% or greater sequence identity with an amino acid sequence selected from the group consisting of amino acids 26–110 of SEQ ID NO:2, amino acids 26–111 of SEQ ID NO:4, and amino acids 26–111 of SEQ ID NO:6.

23. A method of claim 13 wherein said MGF polypeptide comprises an amino acid so once which has 90% or greater sequence identity with an amino acid sequence selected from the group consisting of amino acids 26–110 of SEQ ID NO:2, amino acids 26–111 of SEQ ID NO:4, and amino acids 26–111 of SEQ ID NO:6.

* * * * *

SEQUENCE LISTING

<160> NUMBER OF SEQ ID NOS: 14

<210> SEQ ID NO 1
<211> LENGTH: 517

-continued

```
<212> TYPE: DNA
<213> ORGANISM: Homo sapiens

<400> SEQUENCE: 1
ggaccggaga cgctctgcgg ggctgagctg gtggatgctc ttcagttcgt gtgtggagac      60
aggggctttt atttcaacaa gcccacaggg tatggctcca gcagtcggag ggcgcctcag     120
acaggcatcg tggatgagtg ctgcttccgg agctgtgatc taaggaggct ggagatgtat     180
tgcgcacccc tcaagcctgc caagtcagct cgctctgtcc gtgcccagcg ccacaccgac     240
atgcccaaga cccagaagta tcagccccca tctaccaaca agaacacgaa gtctcagaga     300
aggaaaggaa gtacatttga agaacacaag tagagggagt gcaggaaaca agaactacag     360
gatgtagaag acccttctga ggagtgaaga aggacaggcc accgcaggac cctttgctct     420
gcacagttac ctgtaaacat tggaataccg gccaaaaaat aagtttgatc acatttcaaa     480
gatggcattt cccccaatga aatacacaag taaacat                              517

<210> SEQ ID NO 2
<211> LENGTH: 110
<212> TYPE: PRT
<213> ORGANISM: Homo sapiens

<400> SEQUENCE: 2

Gly Pro Glu Thr Leu Cys Gly Ala Glu Leu Val Asp Ala Leu Gln Phe
  1               5                  10                  15

Val Cys Gly Asp Arg Gly Phe Tyr Phe Asn Lys Pro Thr Gly Tyr Gly
                 20                  25                  30

Ser Ser Ser Arg Arg Ala Pro Gln Thr Gly Ile Val Asp Glu Cys Cys
             35                  40                  45

Phe Arg Ser Cys Asp Leu Arg Arg Leu Glu Met Tyr Cys Ala Pro Leu
         50                  55                  60

Lys Pro Ala Lys Ser Ala Arg Ser Val Arg Ala Gln Arg His Thr Asp
 65                  70                  75                  80

Met Pro Lys Thr Gln Lys Tyr Gln Pro Pro Ser Thr Asn Lys Asn Thr
                 85                  90                  95

Lys Ser Gln Arg Arg Lys Gly Ser Thr Phe Glu Glu His Lys
            100                 105                 110

<210> SEQ ID NO 3
<211> LENGTH: 539
<212> TYPE: DNA
<213> ORGANISM: Rattus sp.

<400> SEQUENCE: 3
ggaccagaga ccctttgcgg ggctgagctg gtggacgctc ttcagttcgt gtgtggacca      60
aggggctttt acttcaacaa gcccacagtc tatggctcca gcattcggag ggcaccacag     120
acgggcattg tggatgagtg ttgcttccgg agctgtgatc tgaggaggct ggagatgtac     180
tgtgtccgct gcaagcctac aaagtcagct cgttccatcc gggcccagcg ccacactgac     240
atgcccaaga ctcagaagtc ccagccccta tcgacacaca agaaaaggaa gctgcaaagg     300
agaaggaaag gaagtacact tgaagaacac aagtagagga agtgcaggaa acaagaccta     360
cagaatgtag gaggagcctc ccgaggaaca gaaaatgcca cgtcaccgca agatcctttg     420
ctgcttgagc aacctgcaaa acatcggaac acctgccaaa tatcaataat gagttcaata     480
tcatttcaga gatgggcatt tccctcaatg aaatacacaa gtaaacattc ccggaattc      539

<210> SEQ ID NO 4
```

<211> LENGTH: 111
<212> TYPE: PRT
<213> ORGANISM: Rattus sp.

<400> SEQUENCE: 4

Gly Pro Glu Thr Leu Cys Gly Ala Glu Leu Val Asp Ala Leu Gln Phe
1               5                   10                  15

Val Cys Gly Pro Arg Gly Phe Tyr Phe Asn Lys Pro Thr Val Tyr Gly
            20                  25                  30

Ser Ser Ile Arg Arg Ala Pro Gln Thr Gly Ile Val Asp Glu Cys Cys
        35                  40                  45

Phe Arg Ser Cys Asp Leu Arg Leu Glu Met Tyr Cys Val Arg Cys
    50                  55                  60

Lys Pro Thr Lys Ser Ala Arg Ser Ile Arg Ala Gln Arg His Thr Asp
65                  70                  75                  80

Met Pro Lys Thr Gln Lys Ser Gln Pro Leu Ser Thr His Lys Lys Arg
                85                  90                  95

Lys Leu Gln Arg Arg Lys Gly Ser Thr Leu Glu Glu His Lys
            100                 105                 110

<210> SEQ ID NO 5
<211> LENGTH: 523
<212> TYPE: DNA
<213> ORGANISM: Oryctolagus cuniculus

<400> SEQUENCE: 5
ggaccggaga cgctctgcgg tgctgagctg gtggatgctc ttcagttcgt gtgtggagac      60
agggcttttt atttcaacaa gcccacagga tacggctcca gcagtcggag ggcacctcag     120
acaggcatcg tggatgagtg ctgcttccgg agctgtgatc tgaggaggct ggagatgtac     180
tgtgcacccc tcaagccggc aaaggcagcc cgctccgtcc gtgcccagcg ccacaccgac     240
atgcccaaga ctcagaagta tcagcctcca tctaccaaca agaaaatgaa gtctcagagg     300
agaaggaaag gaagtacatt tgaagaacac aagtagaggg agtgcaggaa acaagaacta     360
caggatgtag gaagaccctt ctgaggagtg aagaaggaca ggccaccgca ggacccttttg    420 ctctgcacag ttacctgtaa acattggaat accggccaaa aaataagttt gatcacattt     480
caaagatggc atttccccca atgaaataca caagtaaaca ttc                       523

<210> SEQ ID NO 6
<211> LENGTH: 111
<212> TYPE: PRT
<213> ORGANISM: Oryctolagus cuniculus

<400> SEQUENCE: 6

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
        35                  40                  45

Phe Arg Ser Cys Asp Leu Arg Arg Leu Glu Met Tyr Cys Ala Pro Leu
    50                  55                  60

Lys Pro Ala Lys Ala Ala Arg Ser Val Arg Ala Gln Arg His Thr Asp
65                  70                  75                  80

Met Pro Lys Thr Gln Lys Tyr Gln Pro Pro Ser Thr Asn Lys Lys Met
                85                  90                  95

```
Lys Ser Gln Arg Arg Lys Gly Ser Thr Phe Glu Glu His Lys
            100                 105                 110
```

<210> SEQ ID NO 7
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gccaccatgg                                                          10

<210> SEQ ID NO 8
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gcccccatgg                                                          10

<210> SEQ ID NO 9
<211> LENGTH: 318
<212> TYPE: DNA
<213> ORGANISM: Homo sapiens

<400> SEQUENCE: 9
ggaccggaga cgctctgcgg ggctgagctg gtggatgctc ttcagttcgt gtgtggagac    60
aggggctttt atttcaacaa gcccacaggg tatggctcca gcagtcggag ggcgcctcag   120
acaggcatcg tggatgagtg ctgcttccgg agctgtgatc taaggaggct ggagatgtat   180
tgcgcacccc tcaagcctgc caagtcagct cgctctgtcc gtgcccagcg ccacaccgac   240
atgcccaaga cccagaagga agtacatttg aagaacgcaa gtagagggag tgcaggaaac   300
aagaactaca ggatgtag                                                 318

<210> SEQ ID NO 10
<211> LENGTH: 105
<212> TYPE: PRT
<213> ORGANISM: Homo sapiens

<400> SEQUENCE: 10

```
Gly Pro Glu Thr Leu Cys Gly Ala Glu Leu Val Asp Ala Leu Gln Phe
 1               5                  10                  15

Val Cys Gly Asp Arg Gly Phe Tyr Phe Asn Lys Pro Thr Gly Tyr Gly
                20                  25                  30

Ser Ser Ser Arg Arg Ala Pro Gln Thr Gly Ile Val Asp Glu Cys Cys
            35                  40                  45

Phe Arg Ser Cys Asp Leu Arg Arg Leu Glu Met Tyr Cys Ala Pro Leu
        50                  55                  60

Lys Pro Ala Lys Ser Ala Arg Ser Val Arg Ala Gln Arg His Thr Asp
65                  70                  75                  80

Met Pro Lys Thr Gln Lys Glu Val His Leu Lys Asn Ala Ser Arg Gly
                85                  90                  95

Ser Ala Gly Asn Lys Asn Tyr Arg Met
            100                 105
```

<210> SEQ ID NO 11
<211> LENGTH: 487
<212> TYPE: DNA
<213> ORGANISM: Rattus sp.

<400> SEQUENCE: 11

| | | | | | |
|---|---|---|---|---|---|
| ggaccagaga | cccttgcgg | ggctgagctg | gtggacgctc | ttcagttcgt | gtgtggacca | 60 |
| agggcttttt | acttcaacaa | gcccacagtc | tatggctcca | gcattcggag | ggcaccacag | 120 |
| acgggcattg | tggatgagtg | ttgcttccgg | agctgtgatc | tgaggaggct | ggagatgtac | 180 |
| tgtgtccgct | gcaagcctac | aaagtcagct | cgttccatcc | gggcccagcg | ccacactgac | 240 |
| atgcccaaga | ctcagaagga | agtacacttg | aagaacacaa | gtagaggaag | tgcaggaaac | 300 |
| aagacctaca | gaatgtagga | ggagcctccc | gaggaacaga | aaatgccacg | tcaccgcaag | 360 |
| atcctttgct | gcttgagcaa | cctgcaaaac | atcggaacac | ctgccaaata | tcaataatga | 420 |
| gttcaatatc | atttcagaga | tgggcatttc | cctcaatgaa | atacacaagt | aaacattccc | 480 |
| ggaattc | | | | | 487 |

<210> SEQ ID NO 12
<211> LENGTH: 105
<212> TYPE: PRT
<213> ORGANISM: Rattus sp.

<400> SEQUENCE: 12

Gly Pro Glu Thr Leu Cys Gly Ala Glu Leu Val Asp Ala Leu Gln Phe
 1               5                  10                  15
Val Cys Gly Pro Arg Gly Phe Tyr Phe Asn Lys Pro Thr Val Tyr Gly
                20                  25                  30
Ser Ser Ile Arg Arg Ala Pro Gln Thr Gly Ile Val Asp Glu Cys Cys
            35                  40                  45
Phe Arg Ser Cys Asp Leu Arg Arg Leu Glu Met Tyr Cys Val Arg Cys
        50                  55                  60
Lys Pro Thr Lys Ser Ala Arg Ser Ile Arg Ala Gln Arg His Thr Asp
    65                  70                  75                  80
Met Pro Lys Thr Gln Lys Glu Val His Leu Lys Asn Thr Ser Arg Gly
                85                  90                  95
Ser Ala Gly Asn Lys Thr Tyr Arg Met
            100                 105

<210> SEQ ID NO 13
<211> LENGTH: 471
<212> TYPE: DNA
<213> ORGANISM: Oryctolagus cuniculus

<400> SEQUENCE: 13

| | | | | | |
|---|---|---|---|---|---|
| ggaccggaga | cgctctgcgg | tgctgagctg | gtggatgctc | ttcagttcgt | gtgtggagac | 60 |
| agggcttttt | atttcaacaa | gcccacagga | tacggctcca | gcagtcggag | ggcacctcag | 120 |
| acaggcatcg | tggatgagtg | ctgcttccgg | agctgtgatc | tgaggaggct | ggagatgtac | 180 |
| tgtgcacccc | tcaagccggc | aaaggcagcc | cgctccgtcc | gtgcccagcg | ccacaccgac | 240 |
| atgcccaaga | ctcagaagga | agtacatttg | aagaacacaa | gtagagggag | tgcaggaaac | 300 |
| aagaactaca | ggatgtagga | agacccttct | gaggagtgaa | gaaggacagg | ccaccgcagg | 360 |
| acccttgct | ctgcacagtt | acctgtaaac | attggaatac | cggccaaaaa | ataagtttga | 420 |
| tcacatttca | agatggcat | ttccccccaat | gaaatacaca | agtaaacatt | c | 471 |

-continued

```
<210> SEQ ID NO 14
<211> LENGTH: 105
<212> TYPE: PRT
<213> ORGANISM: Oryctolagus cuniculus

<400> SEQUENCE: 14

Gly Pro Glu Thr Leu Cys Gly Ala Glu Leu Val Asp Ala Leu Gln Phe
  1               5                  10                  15

Val Cys Gly Asp Arg Gly Phe Tyr Phe Asn Lys Pro Thr Gly Tyr Gly
             20                  25                  30

Ser Ser Ser Arg Arg Ala Pro Gln Thr Gly Ile Val Asp Glu Cys Cys
         35                  40                  45

Phe Arg Ser Cys Asp Leu Arg Arg Leu Glu Met Tyr Cys Ala Pro Leu
     50                  55                  60

Lys Pro Ala Lys Ala Ala Arg Ser Val Arg Ala Gln Arg His Thr Asp
 65                  70                  75                  80

Met Pro Lys Thr Gln Lys Glu Val His Leu Lys Asn Thr Ser Arg Gly
                 85                  90                  95

Ser Ala Gly Asn Lys Asn Tyr Arg Met
                100                 105
```